US012806236B2

(12) United States Patent
Miyako

(10) Patent No.: US 12,806,236 B2
(45) Date of Patent: Nov. 24, 2026

(54) THERAPEUTIC AGENT OR DIAGNOSTIC AGENT FOR CANCER

(71) Applicant: JAPAN ADVANCED INSTITUTE OF SCIENCE AND TECHNOLOGY, Ishikawa (JP)

(72) Inventor: Eijiro Miyako, Ishikawa (JP)

(73) Assignee: JAPAN ADVANCED INSTITUTE OF SCIENCE AND TECHNOLOGY, Ishikawa (JP)

( * ) Notice: Subject to any disclaimer, the term of this patent is extended or adjusted under 35 U.S.C. 154(b) by 476 days.

(21) Appl. No.: 18/017,934

(22) PCT Filed: Jul. 27, 2021

(86) PCT No.: PCT/JP2021/027698

§ 371 (c)(1),
(2) Date: Jan. 25, 2023

(87) PCT Pub. No.: WO2022/025043

PCT Pub. Date: Feb. 3, 2022

(65) Prior Publication Data

US 2023/0277604 A1 Sep. 7, 2023

(30) Foreign Application Priority Data

Jul. 29, 2020 (JP) ................................ 2020-128089

(51) Int. Cl.
*A61K 35/74* (2015.01)
*A61K 41/00* (2020.01)
(Continued)

(52) U.S. Cl.
CPC .............. *A61K 35/74* (2013.01); *A61K 41/00* (2013.01); *A61K 41/0057* (2013.01); *A61N 5/06* (2013.01);
(Continued)

(58) Field of Classification Search
CPC ..... A61P 35/00; A61K 35/74; A61K 49/0004; A61K 49/0097; A61N 5/06; A61N 2005/0659
See application file for complete search history.

(56) References Cited

U.S. PATENT DOCUMENTS

2006/0142260 A1 6/2006 Scherz et al.

FOREIGN PATENT DOCUMENTS

JP 2003-055240 A 2/2003
JP 2006-515836 A 6/2006
WO 2004/045492 A2 6/2004

OTHER PUBLICATIONS

Kwon et al. (2014). "Rhodobacter sphaeroides, a novel tumor-targeting bacteria that emits natural near-infrared fluorescence". Microbiol. Immunol., 58(3):172-179. (Year: 2014).*

(Continued)

*Primary Examiner* — Samira J Jean-Louis
*Assistant Examiner* — Bailey M Morgan
(74) *Attorney, Agent, or Firm* — Greenblum & Bernstein, P.L.C.

(57) ABSTRACT

It is an object of the present invention to provide a therapeutic agent or a diagnostic agent for cancer, which has high selectivity to cancer and also has low toxicity or little side effects. According to the present invention, provided is a therapeutic agent or a diagnostic agent for cancer, comprising photosynthetic bacteria.

1 Claim, 19 Drawing Sheets

(51) Int. Cl.
*A61N 5/06* (2006.01)
*A61P 35/00* (2006.01)

(52) U.S. Cl.
CPC ...... *A61P 35/00* (2018.01); *A61N 2005/0659* (2013.01)

(56) References Cited

OTHER PUBLICATIONS

Peters et al. (2019). "Phototrophic purple bacteria as optoacoustic in vivo reporters of macrophage activity". Nat. Commun., 10: 1191. (Year: 2019).*

National Center for Health Statistics. (2019). "Health, United States, 2019 Appendixes." (Year: 2019).*

Kamal et al. (2009). "Light-activated cytotoxic compounds from Malaysian microorganisms for photodynamic therapy of cancer." Antonie van Leeuwenhoek, 95:179-188. (Year: 2009).*

Kwon et al. (2014). "Rhodobacter sphaeroides, a novel tumor-targeting bacteria that emits natural near-infrared fluorescence." Microbiol. Immunol. 58:172-179. (Year: 2014).*

Extended European Search Report dated Feb. 28, 2024 issued in the European patent application No. 21848142.2.

Larkum et al., "Living off the Sun; chlorophylls, bacteriochlorophylls and rhodopsins," *Photosynthetica,* vol. 56, No. 1, pp. 11-43, 2018.

Masayuki Yokoyama, *Drug Delivery System,* 33(2), pp. 89-97 (2018).

Hisataka Kobayashi, *Drug Delivery System,* 29(4), pp. 274-284 (2014).

Zhou et al., "Tumour-Targeting Bacteria Engineered to Fight Cancer", *Nature Reviews Cancer,* vol. 18, pp. 727-743 (2018).

Kwon et al., "*Rhodobacter sphaeroides,* a Novel Tumor-Targeting Bacteria that Emits Natural Near-Infrared Fluorescence", *Microbial Immunol.,* vol. 58, pp. 172-179 (2014).

Peters et al., "Phototrophic Purple Bacteria as Optoacoustic In Vivo Reporters of Macrophage Activity", *Nature Communications,* vol. 10, No. 1191, pp. 1-9 (2019).

Zhong et al., "Photosynthetic Biohybrid Nanoswimmers System to Alleviate Tumor Hypoxia for FL/PA/MR Imaging-Guided Enhanced Radio-Photodynamic Synergetic Therapy", *Adv. Funct. Mater.,* vol. 30, pp. 1-11 (2020).

Liu et al., "In Situ Photocatalyzed Oxygen Generation with Photosynthetic Bacteria to Enable Robust Immunogenic Photodynamic Therapy in Triple-Negative Breast Cancer", *Adv. Funct. Mater.,* vol. 30, pp. 1-14 (2020).

Zheng et al., "Self-Propelled and Near-Infrared-Phototaxic Photosynthetic Bacteria as Photothermal Agents for Hypoxia-Targeted Cancer Therapy", *ACS Nano,* vol. 15, pp. 1100-1110 (2020).

Yang et al., "Optically Activatable Photosynthetic Bacteria-based Highly Tumor Specific Immunotheranositcs", *Nano Today,* vol. 37, pp. 1-14 (2021).

International Search Report (ISR) and Written Opinion issued in PCT/JP2021/027698, dated Aug. 31, 2021, along with an English translation of the ISR.

International Preliminary Report on Patentability issued in PCT/JP2021/027698, completed Dec. 14, 2021, along with an English translation thereof.

Office Action dated Jun. 5, 2025 issued in European patent application No. 21848142.2.

Office Action dated Jun. 4, 2026 issued in Chinese patent application No. 202180048406.5, with English machine translation.

* cited by examiner

[Fig. 1]
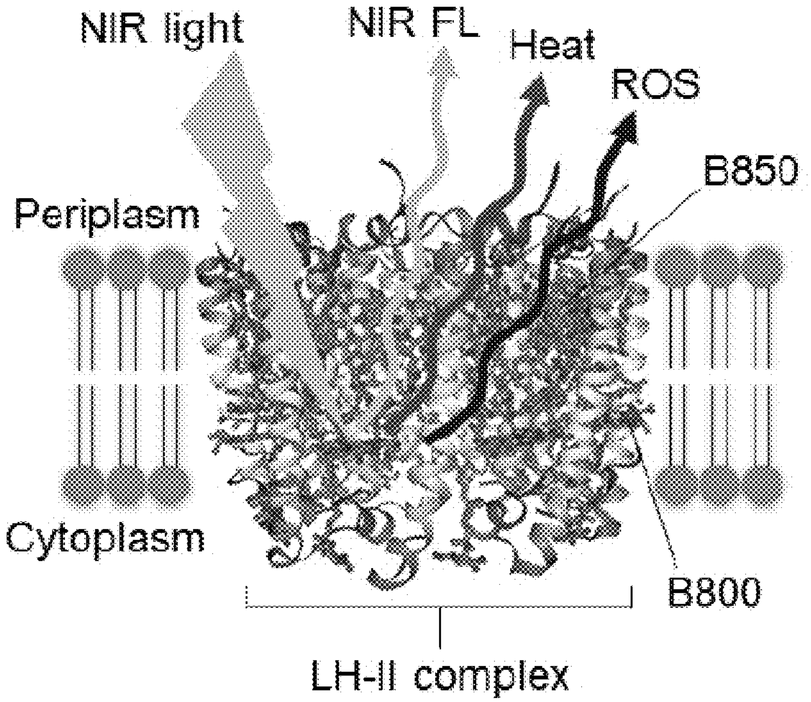
[Fig. 2]
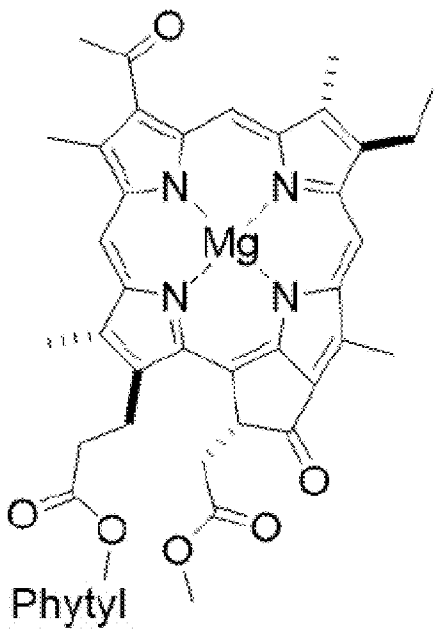

[Fig. 3]
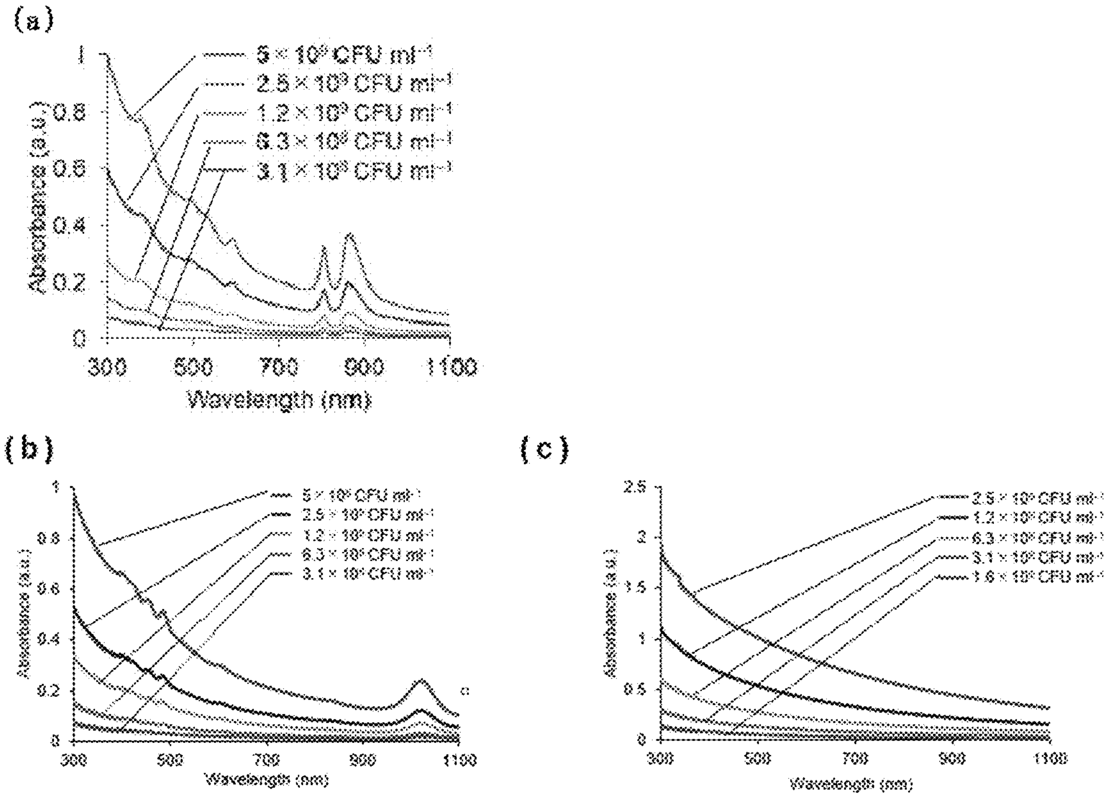
[Fig. 4]
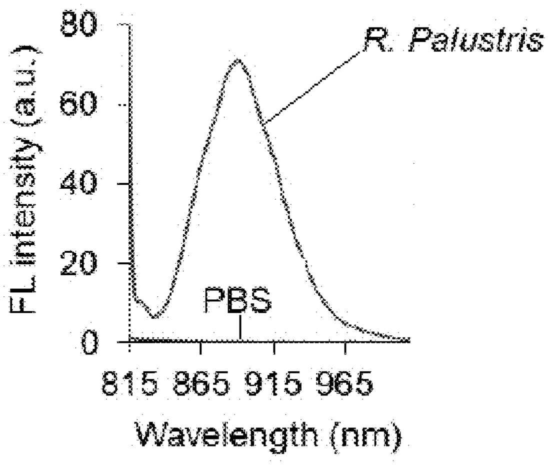

[Fig. 5]
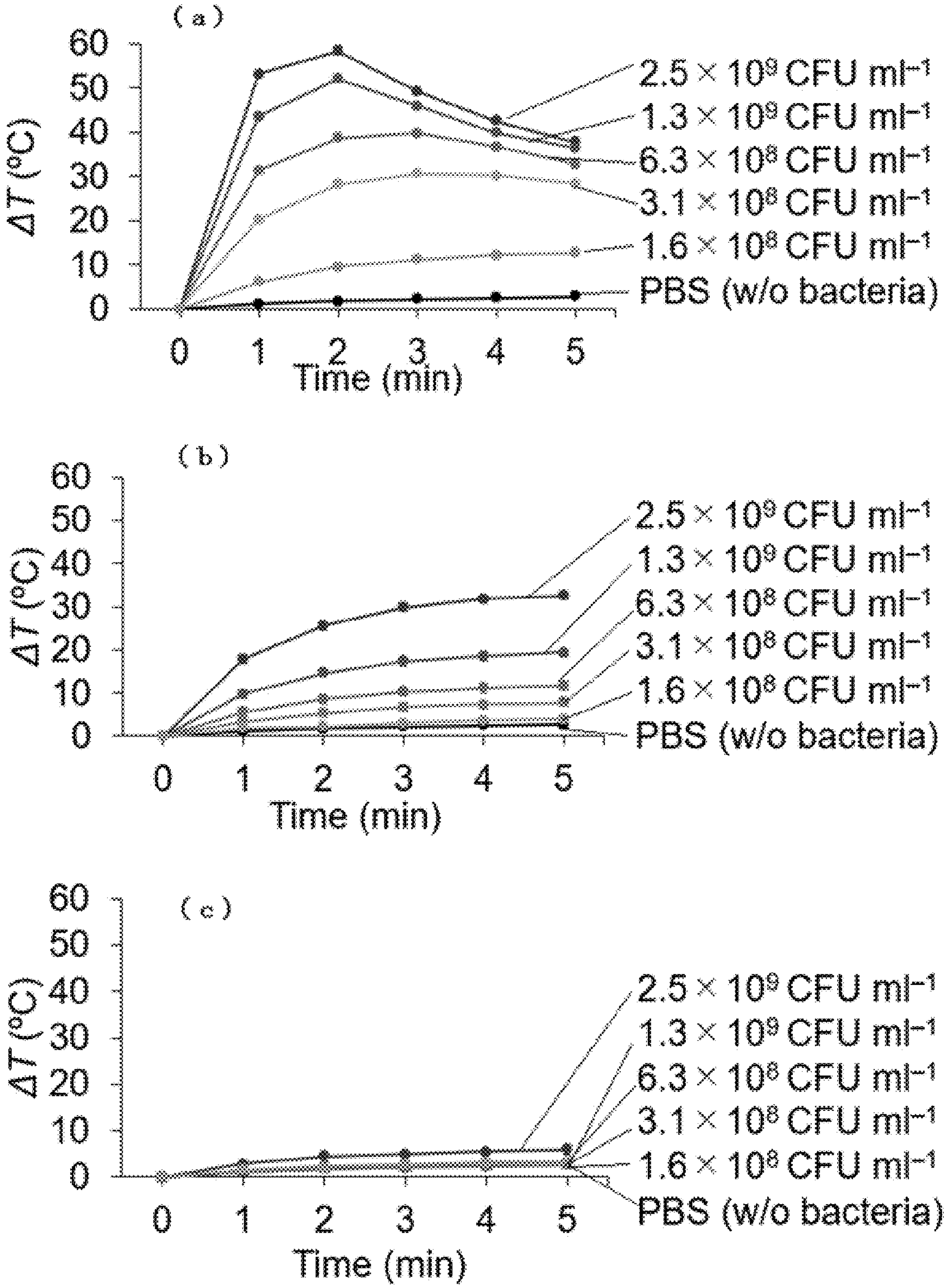

[Fig. 6]
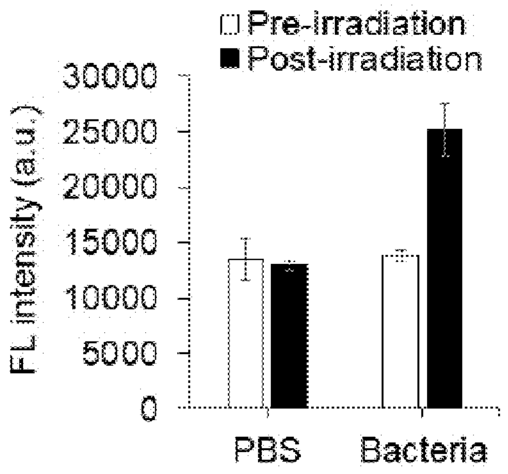
[Fig. 7]
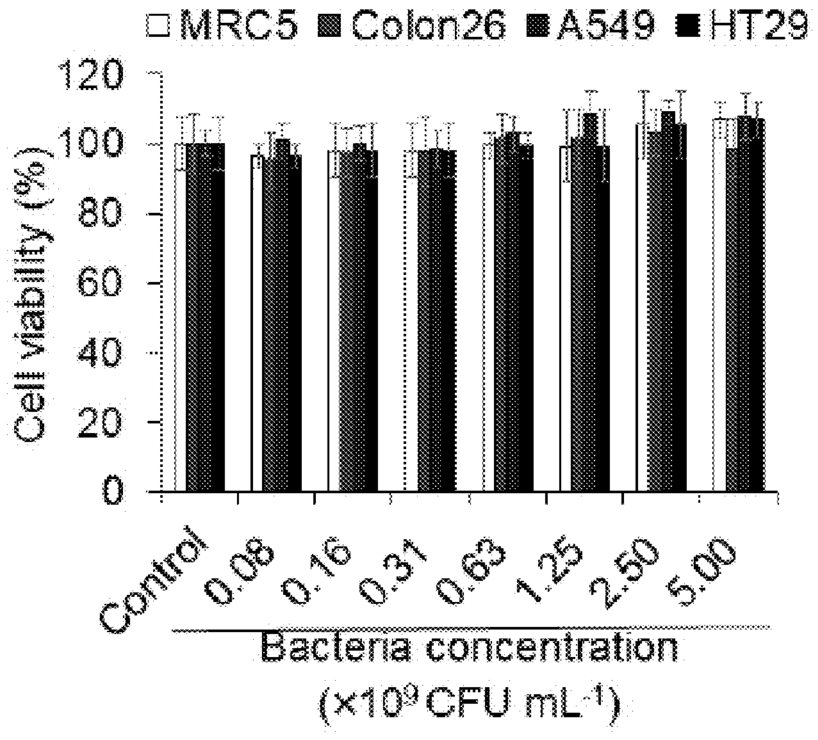

[Fig. 8]
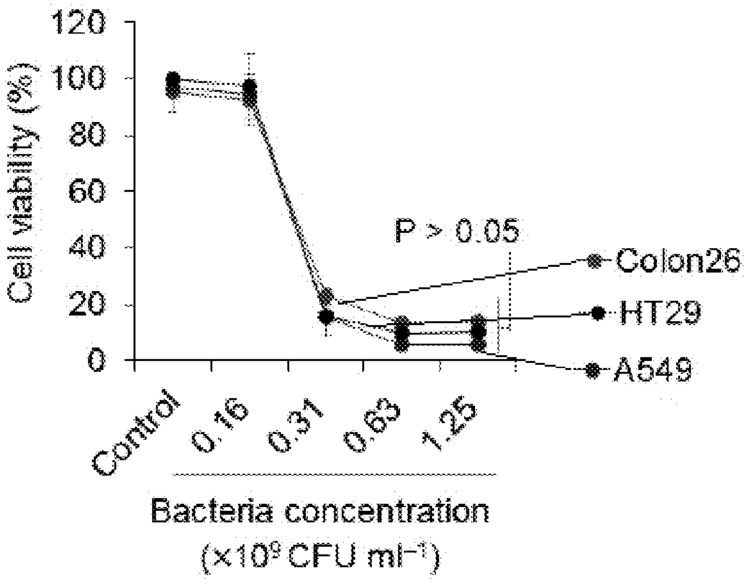
[Fig. 9]
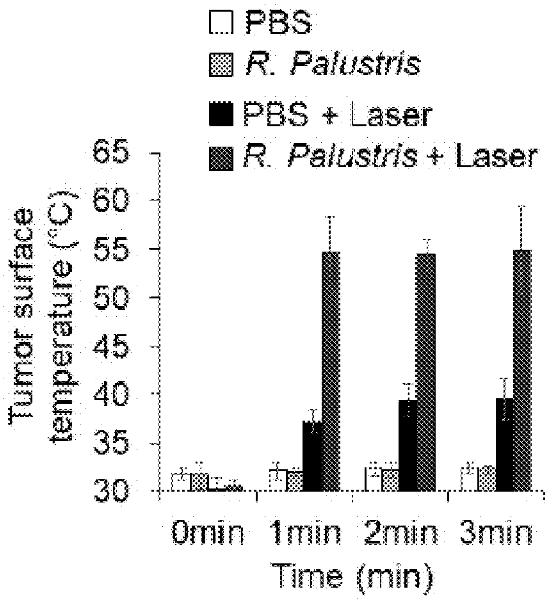

[Fig. 10]
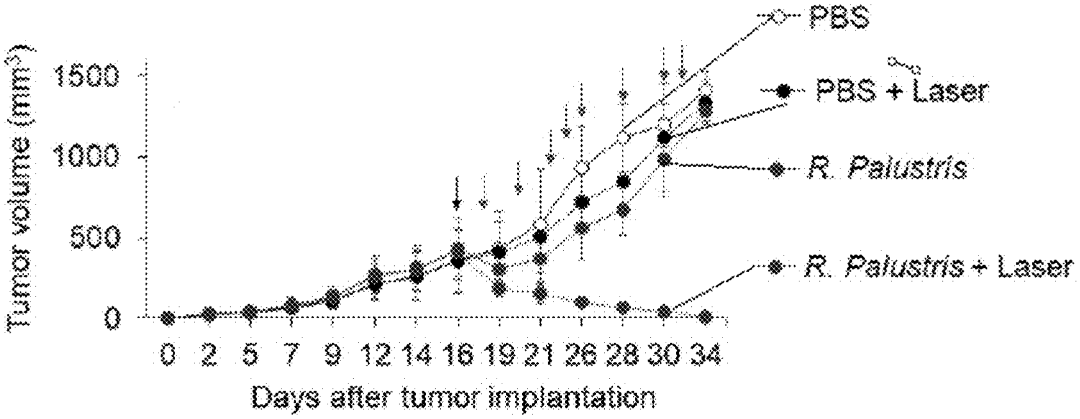
[Fig. 11]
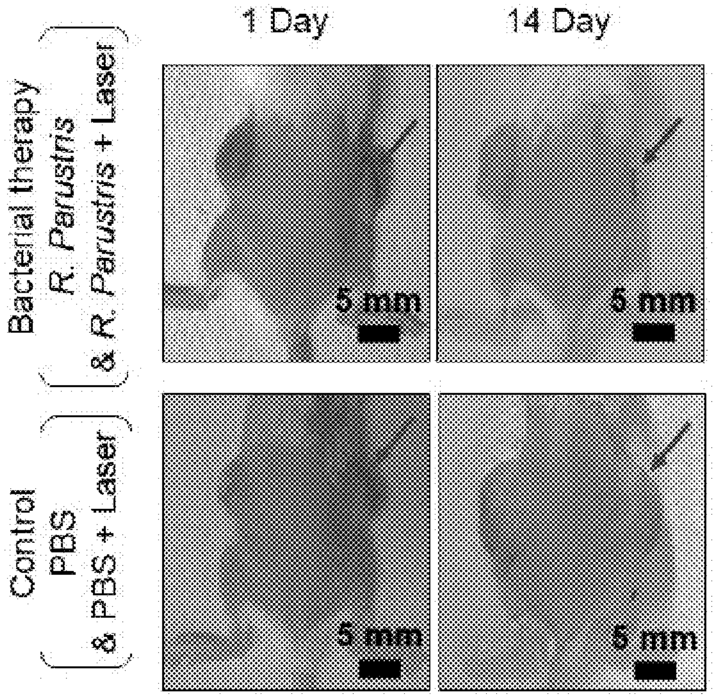

[Fig. 12]
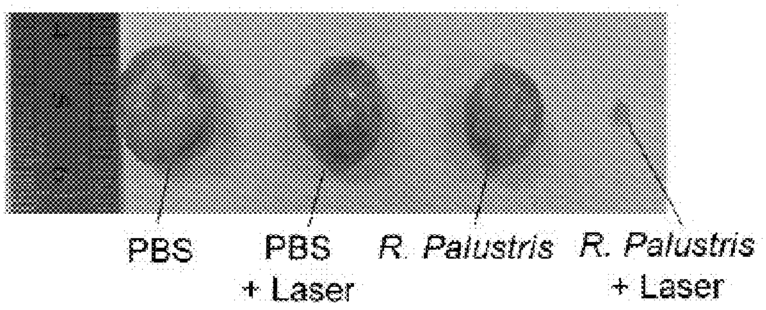
[Fig. 13]
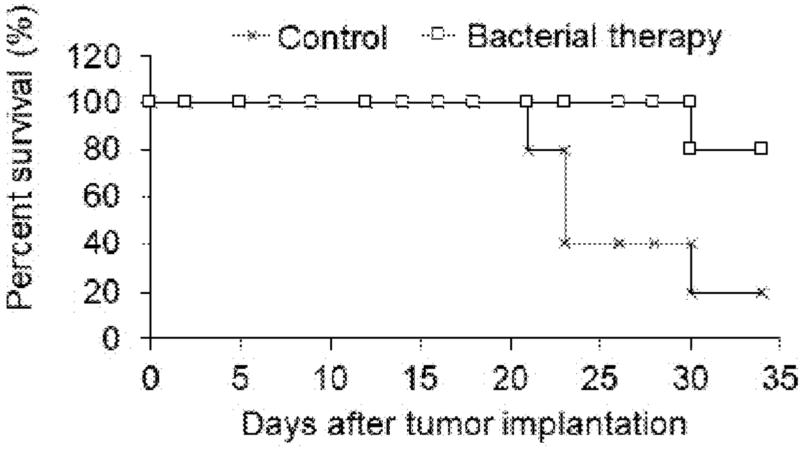

[Fig. 14]
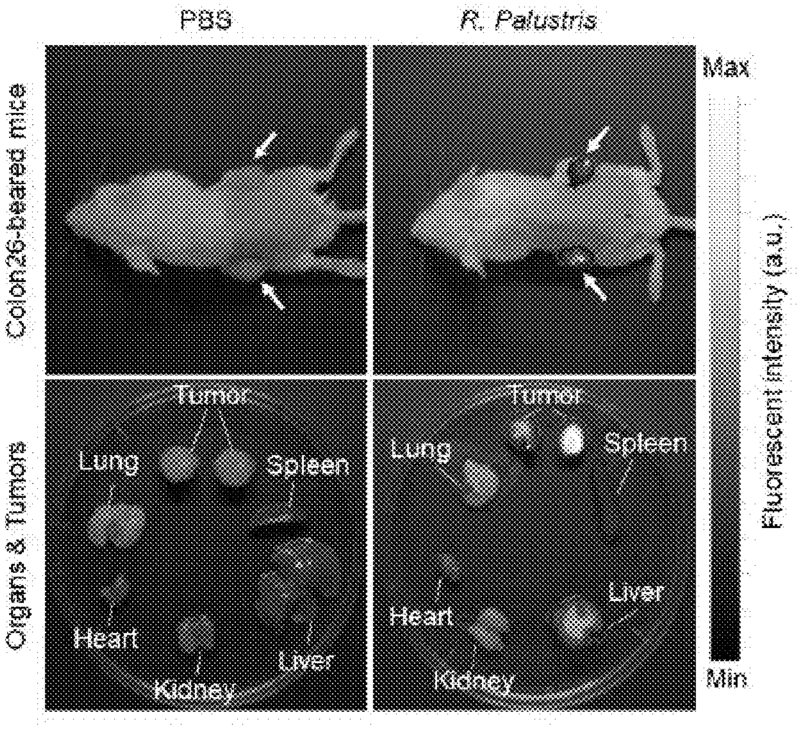
[Fig. 15]
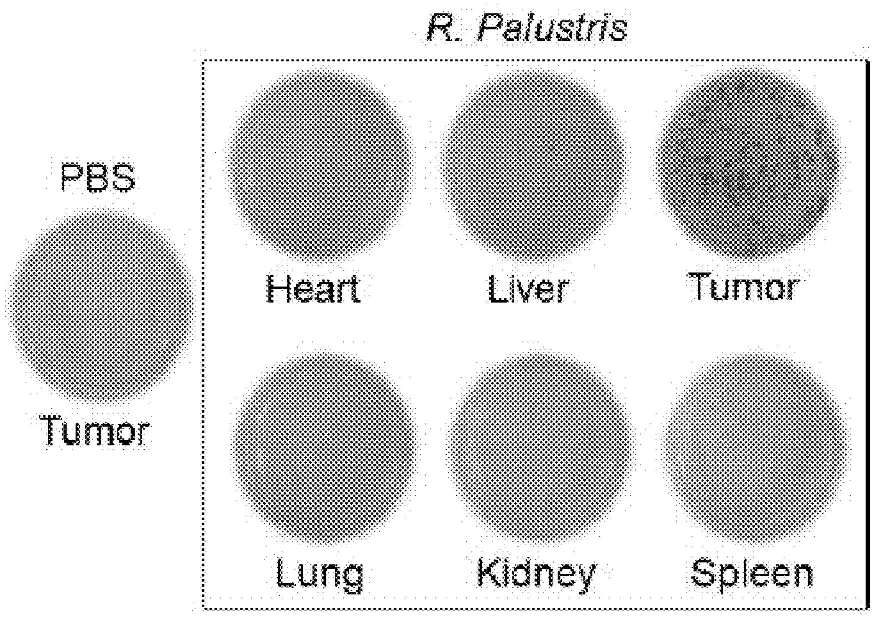

[Fig. 16]
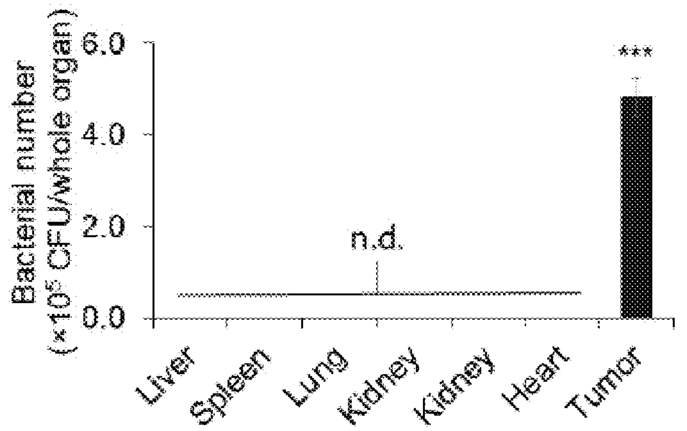
[Fig. 17]
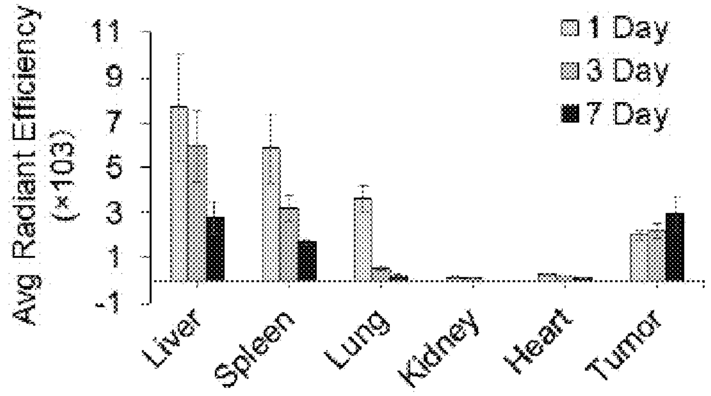
[Fig. 18]
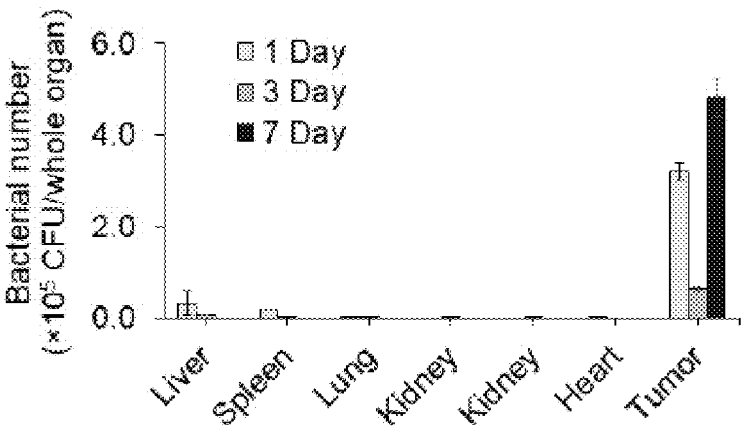

[Fig. 19]
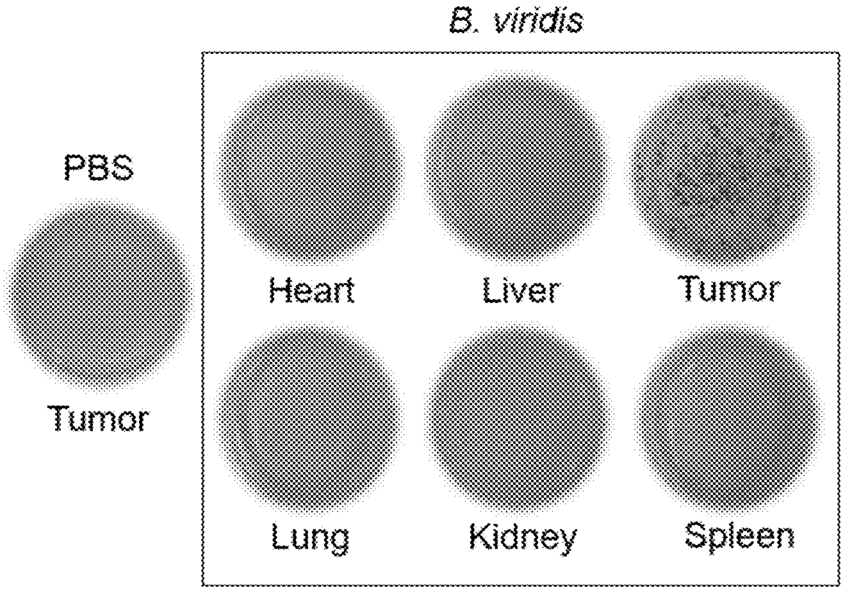
[Fig. 20]
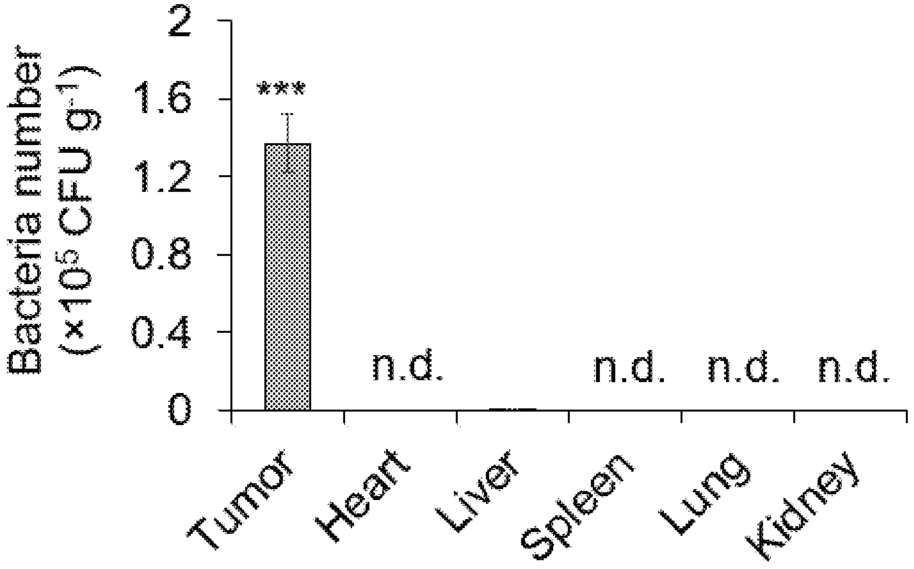

[Fig. 21]
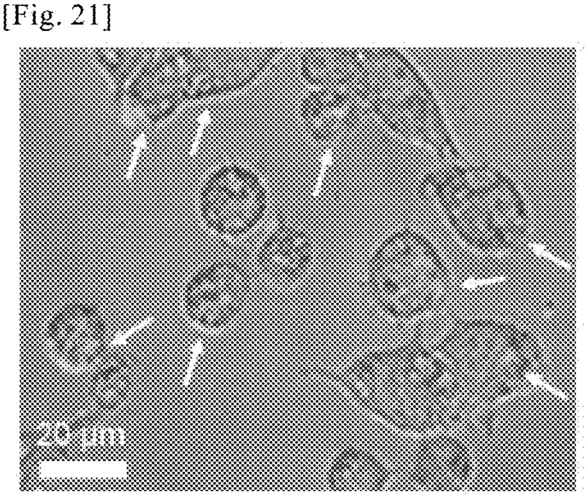
[Fig. 22]
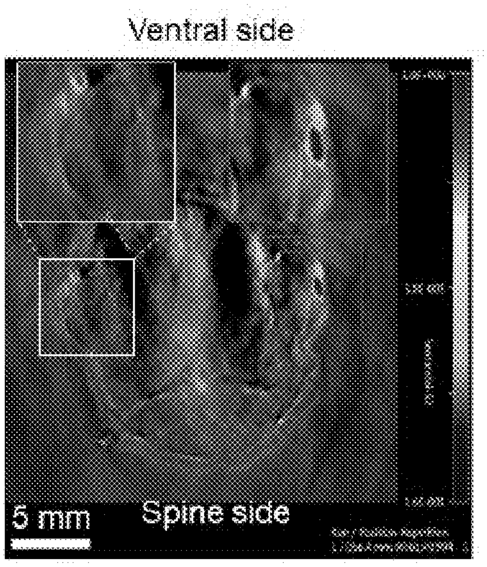
[Fig. 23]
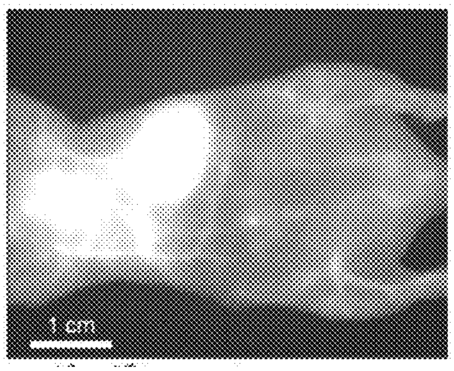

[Fig. 24]
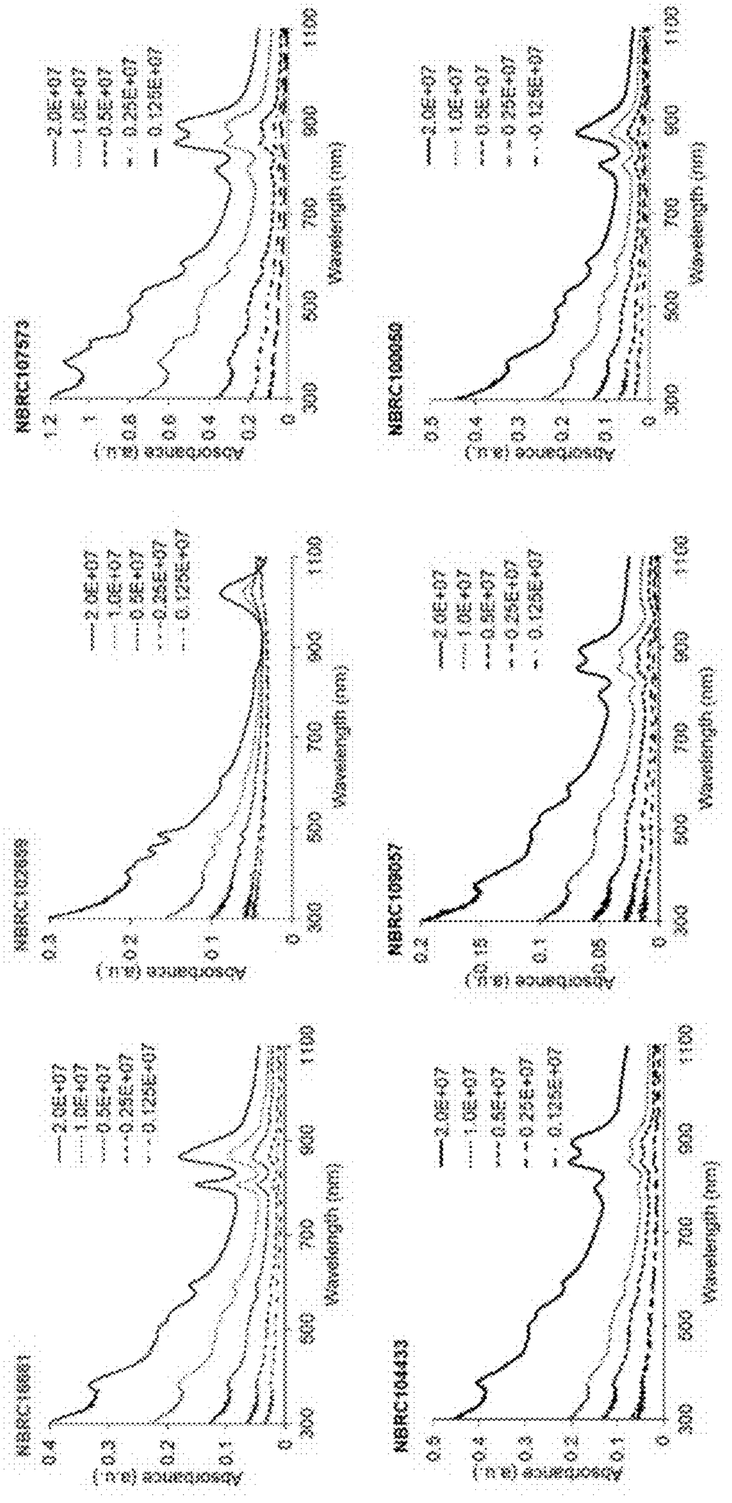

[Fig. 25]
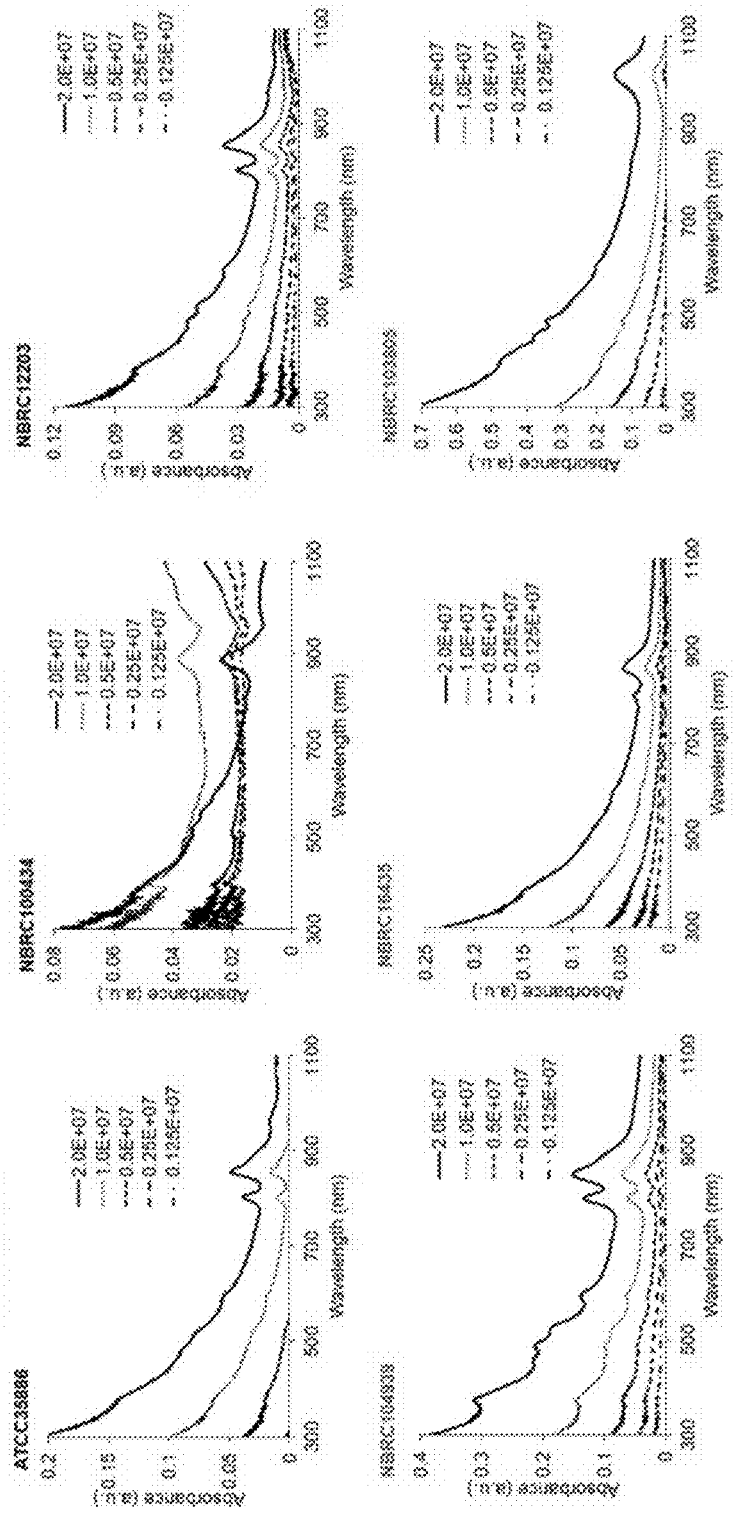

[Fig. 26]
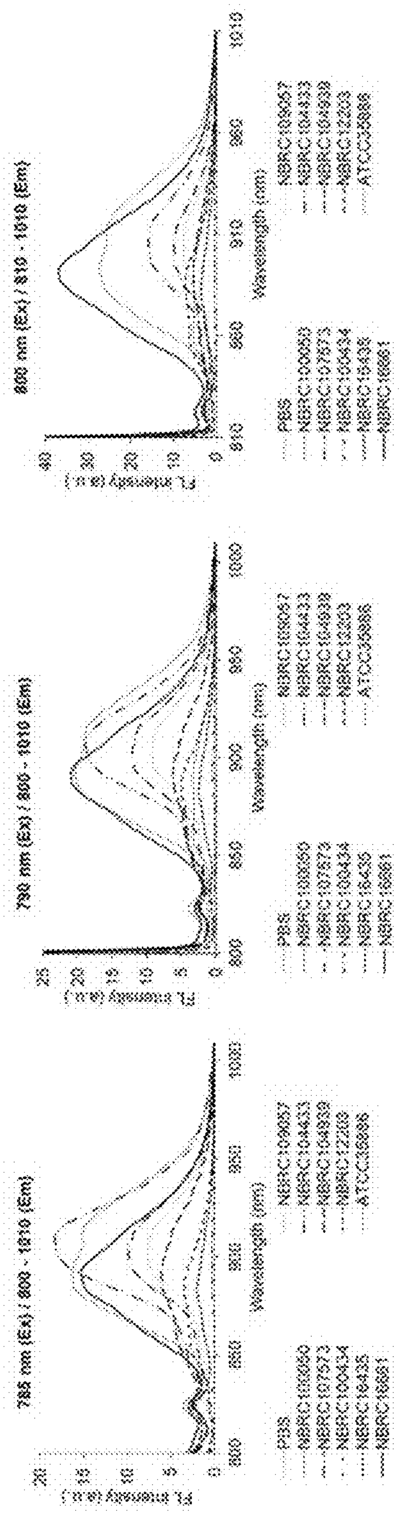

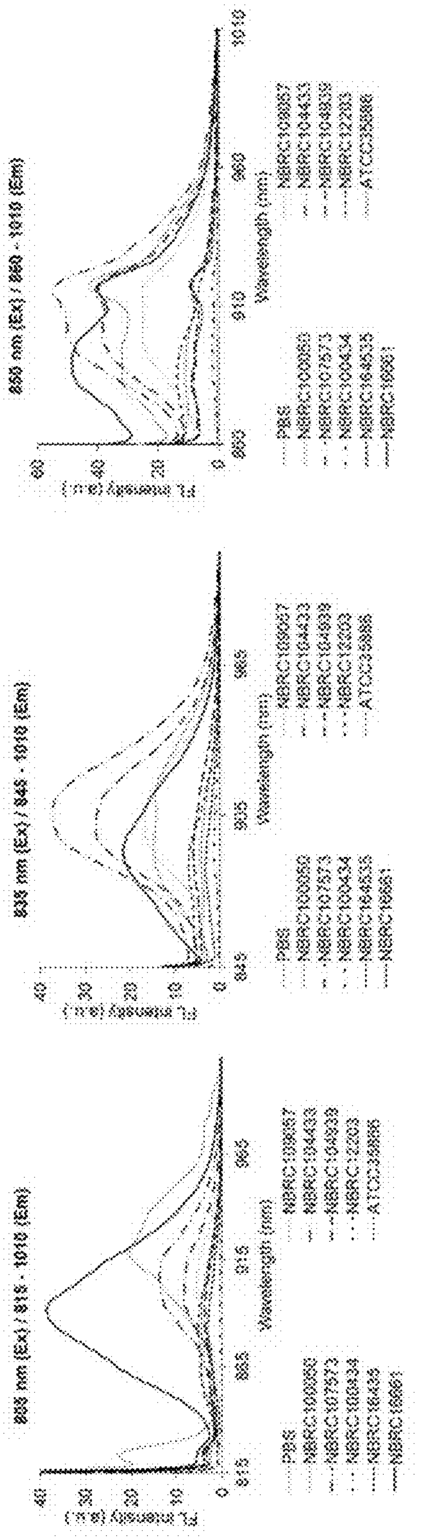
[Fig. 27]

[Fig. 28]
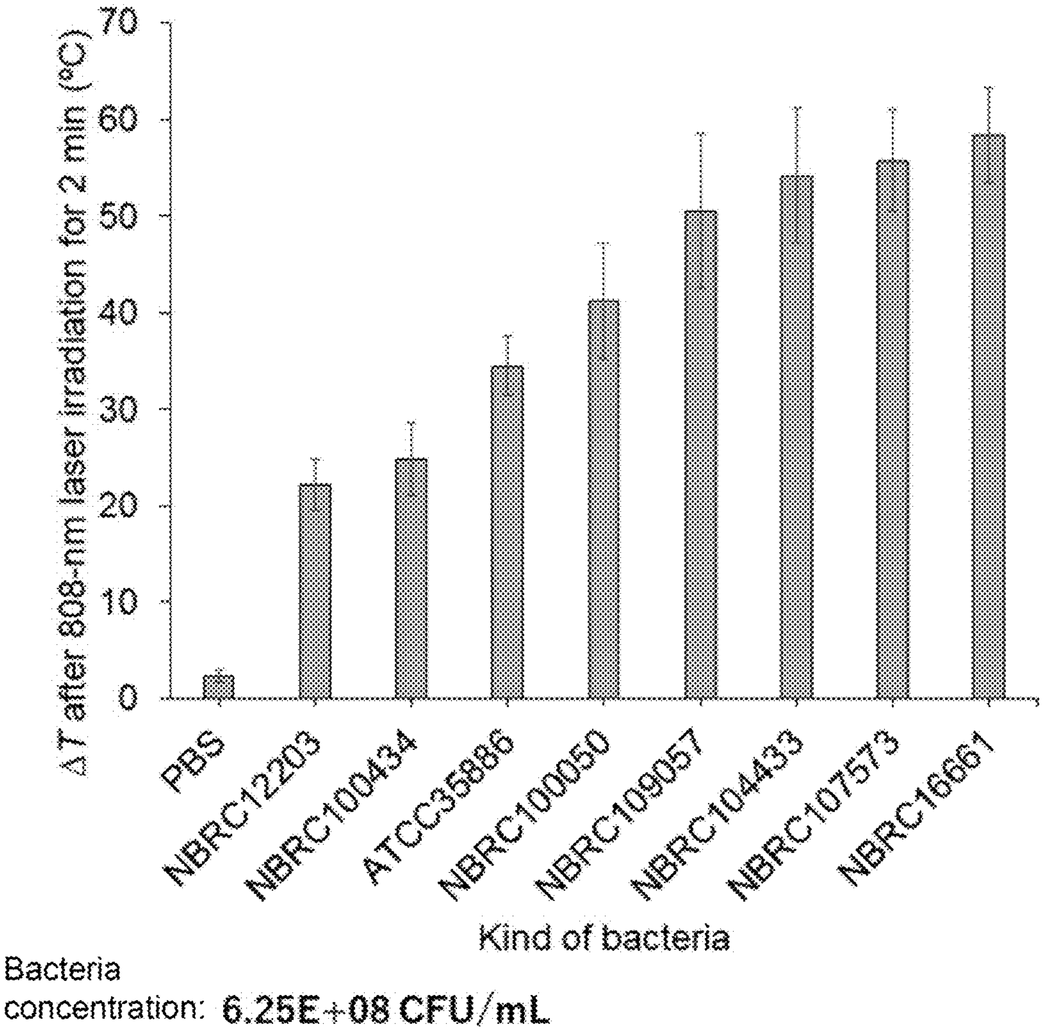

[Fig. 29]
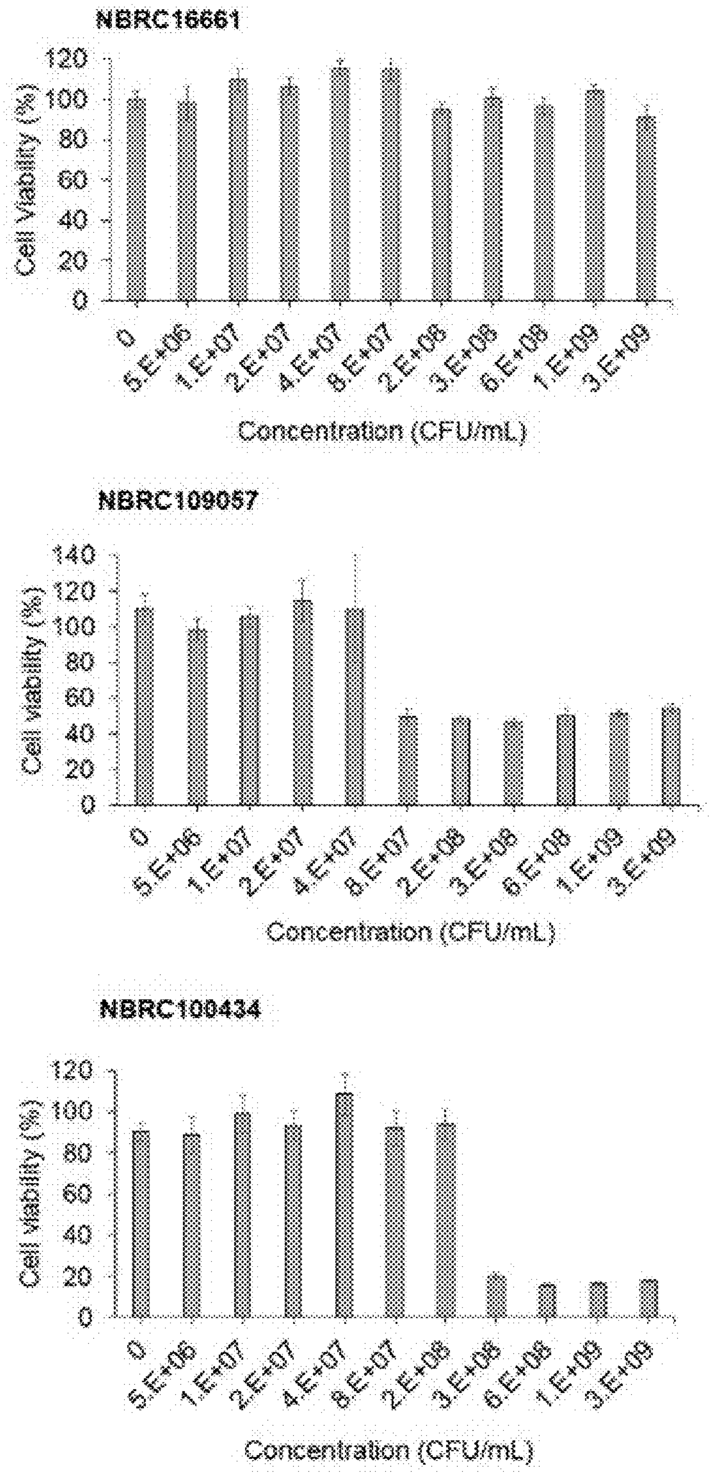

[Fig. 30]
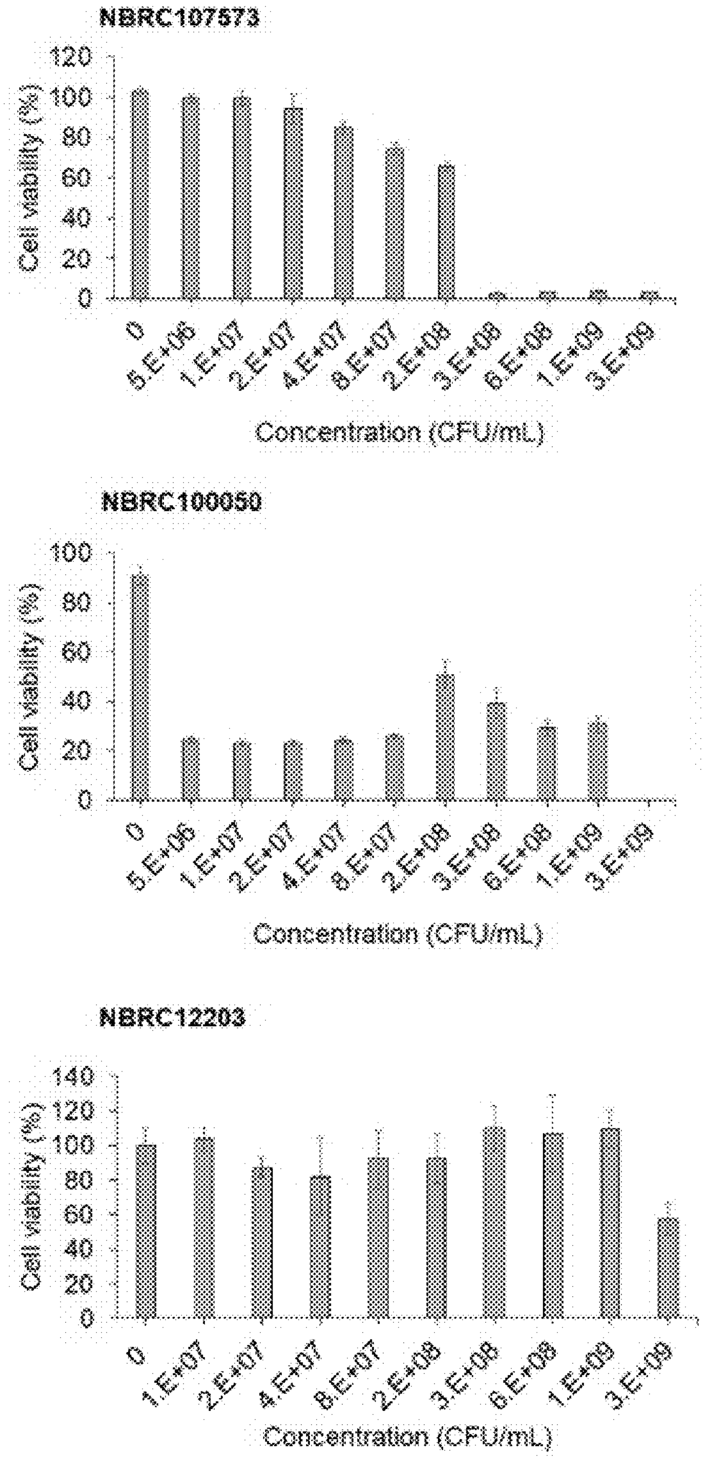

[Fig. 31]
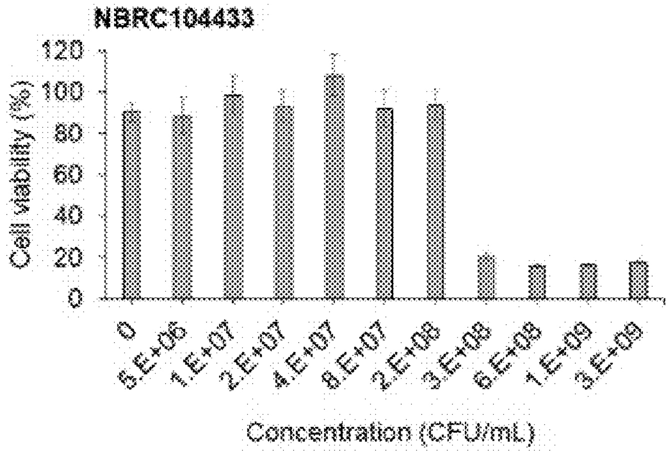
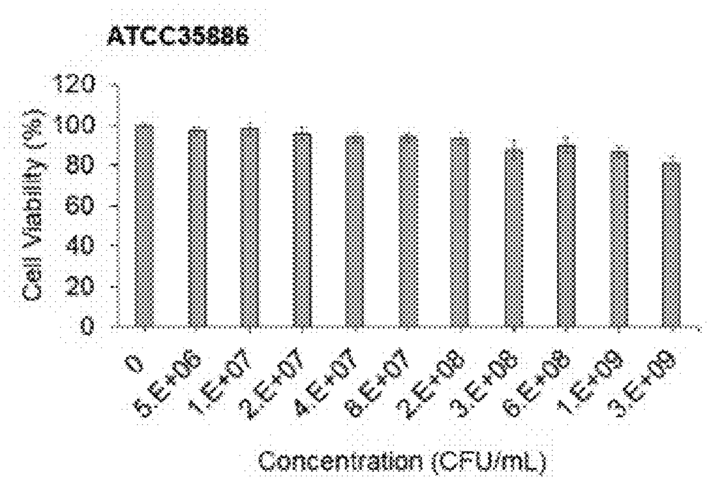

THERAPEUTIC AGENT OR DIAGNOSTIC AGENT FOR CANCER

TECHNICAL FIELD

The present invention relates to a therapeutic agent or a diagnostic agent for cancer, in which photosynthetic bacteria are used.

BACKGROUND ART

Differing from normal vascular endothelial cells, a wide space with a size of about 200 nm is opened between vascular endothelial cells that are present in cancer tissues or inflammatory sites, and thus, nanoparticles whose size is regulated to about 10 to 100 nm are accumulated specifically in cancer tissues. This phenomenon has been known as an "EPR effect" (Enhanced Permeation and Retention Effect). The EPR effect has been frequently cited in study papers regarding a drug delivery system of utilizing nanoparticles, and it has become the greatest support for cancer-selective chemotherapy. On the other hand, there are also many doubts and criticisms concerning the EPR effect. In fact, regarding the EPR effect on solid cancers, there are many environmental factors of inhibiting cancers, such as heterogeneity of blood flow in cancer tissues and a high tissue pressure in the center of cancer, and such a critical defect that the EPR effect itself is not useful has been revealed (for example, Masayuki YOKOYAMA, Drug Delivery System, 33(2), pp. 89-97 (2018)). Moreover, a drug carrier in which the EPR effect is utilized has not been succeeded in human clinical trials, although a long time and high costs have been spent therefor.

Meanwhile, in order to improve tumor-targeting performance, a strategy has been taken to deposit a cancer cell-specific antibody or the like on a drug carrier (for example, Hisataka KOBAYASHI, Drug Delivery System, 29(4), pp. 274-284 (2014)). However, it has been difficult for such an antibody to permeate into a stromal barrier that surrounds a cancer, and thus, sufficient selectivity and medicinal effects could not be obtained. Moreover, since different biomarkers (antigens) are expressed among cancer patients, it is necessary to produce an antibody suitable for each cancer patient in the manner of made-to-order (in an order- (owner-) made manner). However, great time and efforts, and large expenses have been required for the production of an antibody itself, and the resulting enormous medical care costs have been problematic.

In recent years, a cancer target therapy of utilizing anaerobic microorganisms capable of selectively performing accumulation, growth and proliferation in a hypoxic tumor has attracted attention (Shibin Zhou et al. Nature Reviews Cancer, 18, pp. 727-743 (2018)). However, the conventional cancer bacteriotherapy basically has the concept of a so-called drug delivery system involving the delivery of anticancer agents. Moreover, for the expression of anticancer activity, the operation and/or modification of microorganisms needs to be performed using genetic engineering techniques. As a result, the cancer bacteriotherapy is likely to cause unpredictable and uncontrollable problems such as acquisition of drug resistance by bacterial. Furthermore, in many cases, the used bacteria are *salmonella* and *Escherichia coli*, which have been attenuated by genetic modification, and thus, these bacteria always involve the risk of becoming highly toxic again in bodies.

engineering

PRIOR ART DOCUMENTS

Non-Patent Documents

Non-Patent Document 1: Masayuki YOKOYAMA, Drug Delivery System, 33(2), pp. 89-97 (2018)

Non-Patent Document 2: Hisataka KOBAYASHI, Drug Delivery System, 29(4), pp. 274-284 (2014)

Non-Patent Document 3: Shibin Zhou et al. Nature Reviews Cancer, 18, pp. 727-743 (2018)

SUMMARY OF INVENTION

Object to be Solved by the Invention

Nanomedicine has been problematic in that: (1) the nanomedicine depends on the EPR effect as an unclear mechanism, and has low selectivity to cancer; (2) the nanomedicine uses anticancer agents having strong side effects; (3) it requires great time and efforts and high costs for the synthesis thereof; and (4) since the inside of a tumor is a state of oxygen deficiency, a photodynamic therapy-type nanomedicine has low effects.

Antibody therapy has been problematic in that: (1) it is necessary to produce antibodies with respect to biomarkers whose expression levels are different among cancer patients in the manner of made-to-order; (2) since an antibody cannot permeate into a cancer stromal barrier (and binds to only the surface of a tumor), immunocytes are utilized, but it is difficult to eliminate cancer cells from a deep seated tumor; and (3) it requires great time and efforts and high costs for the production.

Conventional bacteriotherapy has been problematic in that: (1) since *salmonella, Listeria monocytogenes*, or *Escherichia coli*, which have been attenuated by genetic modification, are utilized, these bacteria involve the risk of becoming highly toxic (back mutation) again in bodies, and the bacteria are likely to acquire drug resistance as a result of genetic modification; and (2) the conventional bacteriotherapy is a passive drug delivery and requires complicated gene designing.

It is an object of the present invention to provide a therapeutic agent and a diagnostic agent for cancer, which have high selectivity to cancer and also have low toxicity and little side effects.

Means for Solving the Object

As a result of intensive studies conducted directed towards achieving the aforementioned object, the present inventors have found that a therapeutic agent and a diagnostic agent for cancer, which have high selectivity to cancer and also have low toxicity and little side effects, can be provided by using photosynthetic bacteria, which are capable of highly selectively performing accumulation, growth and proliferation in a hypoxic tumor environment and function by irradiation with a highly biopermeable near infrared light, thereby completing the present invention.

Specifically, the present invention is as follows.

<1> A therapeutic agent or a diagnostic agent for cancer, comprising photosynthetic bacteria.

<2> The therapeutic agent or the diagnostic agent for cancer according to <1>, wherein the photosynthetic bacteria are photosynthetic bacteria having a bacteriochlorophyll.

<3> The therapeutic agent or the diagnostic agent for cancer according to <1> or <2>, wherein the photosynthetic bacteria are purple photosynthetic bacteria or green photosynthetic bacteria.

<4> The therapeutic agent or the diagnostic agent for cancer according to any one of <1> to <3>, wherein the photosynthetic bacteria are *Rhodopseudomonas* sp. bacteria, *Blastochloris* sp. bacteria, *Afifella* sp. bacteria, *Rhodobacter* sp. bacteria, *Pararhodospirillum* sp. bacteria, *Rhodomicrobium* sp. bacteria, *Rhodovulum* sp. bacteria, or *Marichromatium* sp. bacteria.

<5> The therapeutic agent or the diagnostic agent for cancer according to any one of <1> to <4>, which is used in combination of light irradiation.

<6> The therapeutic agent or the diagnostic agent for cancer according to <5>, wherein the light irradiation is irradiation with a near infrared light.

Advantageous Effects of Invention

The therapeutic agent and the diagnostic agent for cancer of the present invention has the following advantages.

According to a clear mechanism derived from hypoxia, immune evasion and chemotaxis, it is possible to express high selectivity to a tumor.

Since an anticancer agent having strong side effects is not used and the used bacteria have low toxicity, side effects and toxicity are low.

The used bacteria are able to infinitely self-replicate, and production costs are inexpensive.

It is possible to express not only a photodynamic mode of using oxygen, but also a heat mode that does not need oxygen, and further, the effect of degenerating cancer can be obtained only by administration of bacteria without using a light.

The bacteria are capable of highly selectively performing accumulation, growth and proliferation in a microenvironment that is common in solid cancers.

The bacterial are capable of performing accumulation, growth and proliferation in deep seated tumors.

High selectivity to tumors can be expressed without needing genetic recombination.

BRIEF DESCRIPTION OF DRAWINGS

FIG. 1 shows a conceptual view of purple photosynthetic bacteria driven by a near infrared light.

FIG. 2 shows the chemical structure of bacteriochlorophyll a (BChl a).

FIG. 3 shows the UV-Vis-NIR light absorption properties of individual bacteria. FIG. 3 (*a*) shows the UV-Vis-NIR light absorption properties of *Rhodopseudomonas Palustris*. FIG. 3 (*b*) shows the UV-Vis-NIR light absorption properties of *Blastochloris viridis*. FIG. 3 (*c*) shows the UV-Vis-NIR light absorption properties of *Bifidobacterium bifidum*.

FIG. 4 shows the fluorescence spectrum of R. *Palustris* (excitation wavelength: 805 nm).

FIG. 5 shows changes in the temperatures of individual bacteria-dispersed solutions during irradiation with a near infrared laser [wavelength: 808 nm, output: 1.2 W (ca. 61.1 $mW/mm^2$), and irradiation time: 5 min]. FIG. 5 (*a*) shows changes in the temperatures of *Rhodopseudomonas Palustris*-dispersed solutions during irradiation with the near infrared laser. FIG. 5(*b*) shows changes in the temperatures of *Blastochloris viridis*-dispersed solutions during irradiation with the near infrared laser. FIG. 5 (*b*) shows changes in the temperatures of *Bifidobacterium bifidum*-dispersed solutions during irradiation with the near infrared laser.

FIG. 6 shows the behavior of generation of reactive oxygen species (ROS) singlet oxygen from an R. *Palustris*-dispersed solution during irradiation with a near infrared laser.

FIG. 7 shows evaluation of the cytotoxicity of the purple photosynthetic bacteria R. *Palustris*.

FIG. 8 shows evaluation of the viability of various types of cancer cells that coexist with a control (a DMEM medium in which no bacteria are present) and with different concentrations of *R. Palustris*, when the cancer cells are irradiated with a near infrared laser.

FIG. 9 shows the measurement of the tumor surface temperature of Colon26 cancer-bearing mouse models during irradiation with a near infrared laser.

FIG. 10 shows evaluation of the antitumor activity of R. *Palustris* that is driven by a near infrared light.

FIG. 11 shows photographs of mice after individual treatments (wherein the arrow indicates each tumor irradiated with a laser).

FIG. 12 shows a photograph of tumors excised 34 days after completion of various types of treatments.

FIG. 13 shows the survival percentage of mice under individual treatments for 34 days.

FIG. 14 shows the fluorescence bioimaging of the in vivo near infrared I region (NIR-I) of Colon26 cancer-bearing mouse models.

FIG. 15 shows a photograph of red colonies derived from R. *Palustris* that has specifically grown in a tumor.

FIG. 16 shows the number of surviving cells of R. *Palustris* in various types of organs and a tumor.

FIG. 17 shows the fluorescent intensity derived from R. *Palustris* in various types of organs and a tumor.

FIG. 18 shows the number of surviving cells of R. *Palustris* in various types of organs and a tumor.

FIG. 19 shows a photograph of green colonies derived from *Blastochloris viridis* that has specifically grown in a tumor.

FIG. 20 shows the number of surviving cells of *Blastochloris viridis* in various types of organs and a tumor.

FIG. 21 shows an NIR-I fluorescence microscope image of mouse macrophages (RAW264.7) that have been co-cultured with *R. Palustris* ($1\times10^8$ CFU/mL) for 4 hours.

FIG. 22 shows a photoacoustic (PA) imaging of a mouse tumor using R. *Palustris*.

FIG. 23 shows angiography according to near infrared II region (NIR-II) fluorescence bioimaging using *Blastochloris viridis*.

FIG. 24 shows the UV-Vis-NIR light absorption properties of individual bacteria.

FIG. 25 shows the UV-Vis-NIR light absorption properties of individual bacteria.

FIG. 26 shows the fluorescence spectra of individual bacteria (bacteria concentration: 2.5E+07 CFU/mL).

FIG. 27 shows the fluorescence spectra of individual bacteria (bacteria concentration: 2.5E+07 CFU/mL).

FIG. 28 shows changes in the temperatures of individual bacteria-dispersed solutions during irradiation with a near infrared laser [wavelength: 808 nm, and irradiation time: 2 min].

FIG. 29 shows evaluation of the cytotoxicity of individual bacteria.

FIG. 30 shows evaluation of the cytotoxicity of individual bacteria.

FIG. 31 shows evaluation of the cytotoxicity of individual bacteria.

EMBODIMENTS OF CARRYING OUT THE INVENTION

The present invention relates to a therapeutic agent or a diagnostic agent for cancer, comprising photosynthetic bacteria.

As photosynthetic bacteria used in the present invention, photosynthetic bacteria having a bacteriochlorophyll is preferable. Examples of the bacteriochlorophyll may include bacteriochlorophyll a, bacteriochlorophyll b, bacteriochlorophyll c, bacteriochlorophyll d, bacteriochlorophyll f, and bacteriochlorophyll g. Photosynthetic bacteria comprising one or more of these bacteriochlorophylls can be used. As an example, photosynthetic bacteria having bacteriochlorophyll a or bacteriochlorophyll b can be used. More specifically, purple photosynthetic bacteria or green photosynthetic bacteria can be used. FIG. 1 shows a conceptual view of purple photosynthetic bacteria driven by a near infrared light. FIG. 2 shows the chemical structure of bacteriochlorophyll a (BChl a).

Examples of the photosynthetic bacteria may include *Rhodopseudomonas* sp. bacteria, *Blastochloris* sp. bacteria, *Afifella* sp. bacteria, *Rhodobacter* sp. bacteria, *Rubrivivax* sp. bacteria, *Pararhodospirillum* sp. bacteria, *Rhodocista* sp. bacteria, *Marichromatium* sp. bacteria, *Phaeochromatium* sp. bacteria, *Rhodoferax* sp. bacteria, *Rhodomicrobium* sp. bacteria, *Thermochromatium* sp. bacteria, *Chlorobaculum* sp. bacteria, and *Rhodovulum* sp. bacteria.

Among the above-described bacteria, *Rhodopseudomonas* sp. bacteria, *Blastochloris* sp. bacteria, *Afifella* sp. bacteria, *Rhodobacter* sp. bacteria, *Pararhodospirillum* sp. bacteria, *Rhodomicrobium* sp. bacteria, *Rhodovulum* sp. bacteria, or *Marichromatium* sp. bacteria are preferable.

Specific examples of the purple photosynthetic bacteria may include *Rhodopseudomonas Palustris, Blastochloris viridis, Afifella marina, Blastochloris sulfoviridis, Rhodobacter blasticus, Rhodobacter capsulatus, Rhodobacter sphaeroides, Rhodopseudomonas pseudopalustris, Rubrivivax gelatinosus, Pararhodospirillum oryzae, Pararhodospirillum sulfurexigens, Rhodocista centenaria, Marichromatium litoris, Phaeochromatium fluminis, Rubrivivax gelatinosus, Rhodoferax fermentans, Rhodomicrobium udaipurense, Rhodomicrobium vannielii*, and *Rhodovulum sulfidophilum.*

Specific examples of the green photosynthetic bacteria may include *Thermochromatium tepidum* and *Chlorobaculum tepidum.*

Among the above-described bacteria, *Rhodopseudomonas Palustris, Blastochloris viridis, Pararhodospirillum oryzae, Pararhodospirillum sulfurexigens, Rhodomicrobium udaipurense, Rhodomicrobium vannielii, Rhodovulum sulfidophilum, Afifella marina, Rhodobacter sphaeroides, Marichromatiurn litoris, Rhodobacter capsulatus*, or *Blastochloris sulfoviridis* are particularly preferable.

The above-described photosynthetic bacteria can be purchased from DSMZ (Deutsche Sammlung von Mikroorganismen and Zellkulturen GmbH), ATCC (American Type Culture Collection), or the like. Otherwise, in Japan, such photosynthetic bacterial strains are preserved in and are furnished from National BioResource Center (NBRC), National Institute of Technology and Evaluation, which has taken over IFO, or RIKEN BioResource Center. Thus, the photosynthetic bacterial strains are available from these organizations.

DSMZ
https://www.dsmz.de/collection/catalogue/microorganisms

ATCC
https://www.atcc.org/Advanced %20Search.aspx

NBRC
https://www.nite.go.jp/nbrc/cultures/nbrc/index.html

RIKEN BRC
https://jcm.brc.riken.jp/ja/

Other than the above-described organizations, some bacteria can be furnished from laboratories of domestic universities in some cases.

The therapeutic agent or the diagnostic agent for cancer of the present invention can be used in combination with light irradiation. That is to say, photosynthetic bacteria are administered to a subject, the photosynthetic bacteria are then accumulated in an affected area in which a cancer is present, and a light can be applied to the affected area. The photosynthetic bacteria generate fluorescence, heat or singlet oxygen (reactive oxygen species: ROS) as a result of the light irradiation, and the photosynthetic bacteria can thereby kill cancer cells.

Light irradiation can be carried out by laser irradiation. Light irradiation is preferably irradiation with a near infrared light laser. The near infrared light is an electromagnetic wave having a wavelength of about 0.7 to 2.5 μm, and it has a wavelength close to a red visible light.

The wavelength of the near infrared light is not particularly limited, and the wavelength is preferably 700 nm to 2000 nm or 700 nm to 1400 nm, and it may also be 750 nm to 1200 nm, 750 nm to 1000 nm, or 750 nm to 900 nm. As an example, the wavelength of the near infrared light is 808 nm.

The output of the near infrared light may be selected, as appropriate, depending on the wavelength of a light used, etc. The output of the near infrared light can be set to be, for example, 0.5 W or more, preferably 0.7 W or more, and more preferably 1.0 W or more. The upper limit of the output is not particularly limited, and it is generally 20 W or less, and preferably 10 W or less.

The time required for the light irradiation is not particularly limited, as long as the effects of the present invention can be obtained. The light irradiation time is generally 1 minute to 30 minutes, and preferably 1 minute to 20 minutes.

The light irradiation may be carried out only once, or may also be carried out several times such as two or more times.

When photosynthetic bacteria is used as a diagnostic agent, a near infrared fluorescence image may be observed in a subject to which the photosynthetic bacteria are administered. For example, using an excitation wavelength of 740 to 1200 nm, a fluorescence wavelength of 810 to 1500 nm can be observed.

The subject, to which the therapeutic agent or the diagnostic agent for cancer of the present invention is administered, is a human or a non-human mammal (e.g. an experimental animal such as a mouse). The subject is preferably affected with a cancer.

Specific examples of the cancer may include breast cancer, lung cancer, endometrial cancer, ovarian cancer, pancreatic cancer, adrenocortical cancer, non-Hodgkin's lymphoma, multiple myeloma, leukemia, Kaposi's sarcoma, Ewing sarcoma, soft tissue sarcoma, nephroblastoma, glioblastoma, prostate cancer, liver cancer, bone cancer, chondrosarcoma, kidney cancer, bladder cancer, stomach cancer, colon cancer, rectal cancer, thyroid cancer, head and neck cancer, and skin cancer (melanoma, etc.), but examples of the cancer are not particularly limited thereto.

Examples of the method of administering the agent to a subject may include administration involving injections (subcutaneous injection, intramuscular injection, intradermal injection, intraperitoneal injection, intratumoral injection, intravenous injection, etc.), and local administration, but examples of the administration method are not limited thereto. The administration method is preferably administration by intravenous injection.

The injection can be produced according to an ordinary method using pharmaceutically acceptable carriers (e.g. a normal saline, an appropriate buffer solution, etc.).

The applied dose of photosynthetic bacteria can be determined, as appropriate, depending on the conditions of a subject. The applied dose of photosynthetic bacteria is, as a bacterial count, generally $1\times10^7$ CFU/kg to $1\times10^{13}$ CFU/kg, and preferably $1\times10^8$ CFU/kg to $1\times10^{12}$ CFU/kg.

The aforementioned dose can be administered to a subject, once, or as divided doses over several administrations (2, 3, or 4 times, etc.), or in the form of a single preparation.

According to the present invention, the following features of the invention are further provided.

<A1> A method for treating cancer, comprising administering photosynthetic bacteria to a subject.

<A2> The method for treating cancer according to the above <A1>, further comprising applying a light to the subject, to which the photosynthetic bacteria is administered.

<A3> A method for diagnosing a cancer, comprising administering photosynthetic bacteria to a subject.

<B1> photosynthetic bacteria for use in the treatment or diagnosis of cancer.

<B2> The photosynthetic bacteria according to the above <B1>, which is used in combination with light irradiation.

<C1> Use of photosynthetic bacteria for production of a therapeutic agent or a diagnostic agent for cancer.

The present invention will be more specifically described in the following examples. However, these examples are not intended to limit the scope of the present invention.

Examples

<Cell Culture>

The bacteria used in the present study were obtained from National Institute of Technology and Evaluation Biological Resource Center (NBRC), and American Type Culture Collection (ATCC).

*Rhodopseudomonas Palustris* (NBRC16661), *Blastochloris viridis* (NBRC 102659), *Pararhodospirillum oryzae* (NBRC107573), *Pararhodospirillum sulfurexigens* (NBRC104433), *Rhodomicrobium* udaipurense (NBRC109057), *Rhodomicrobium vannielii* (NBRC100050), *Rhodovulum sulfidophilum* (ATCC35886), *Afifella marina* (NBRC100434), *Rhodobacter sphaeroides* (NBRC12203), *Marichromatium litoris* (NBRC104939), *Rhodobacter capsulatus* (NBRC16435), and *Blastochloris sulfoviridis* (NBRC103805) were subjected to an anaerobic culture in a 543 ATCC medium at a temperature of 26 °C to 30 °C, while the bacteria were irradiated with a tungsten lamp. *Bifidobacterium bifidum* (NBRC 100015) was subjected to an anaerobic culture in a 385NBRC medium at a temperature of 37 °C.

The reagents utilized in the cell culture were obtained from FUJIFILM Wako Pure Chemical.

<Analysis of Optical Properties of Bacteria>

The absorption spectrum of a bacteria-dispersed solution was measured at room temperature, using a UV-Vis-NIR spectrophotometer (V-730 BIO; Jasco). The fluorescence of such a bacteria-dispersed solution was measured using fluorescence spectrometers (FP-8600 NIR Spectrofluorometer, Jasco; or Fluorolog-3, HORIBA Jobin Yvon).

The UV-Vis-NIR light absorption properties of individual bacteria ((a) *Rhodopseudomonas Palustris*, (b) *Blastochloris viridis*, and (c) *Bifidobacterium bifidum*) are shown in FIG. 3. In addition, the UV-Vis-NIR light absorption properties of individual bacteria are also shown in FIG. 24 and FIG. 25. These are the results obtained by performing the measurement while the bacteria concentration was fixed.

The fluorescence spectrum (excitation wavelength: 805 nm) of *R. Palustris* is shown in FIG. 4. In addition, the fluorescence spectra of individual bacteria when the excitation wavelength and the fluorescence wavelength were changed are shown in FIG. 26 and FIG. 27.

<Temperature Measurement>

A change in the temperature of a bacteria-dispersed solution irradiated with a laser was examined by the following method. That is, a fiber cup-type continuous wave laser with a wavelength of 808 nm (laser spot diameter: about 5 mm; output: 1.2 W, about 61.1 mW mm 2; CivilLaser) was applied to a PBS buffer solution (100 μL) in which bacteria were dispersed, or a PBS buffer solution (100 μL) in which no bacteria were dispersed. A change in the temperature of the solution during the laser irradiation was measured using a temperature sensor (AD-5601A; A & D).

Changes in the temperatures of the dispersed solutions of individual bacteria ((a) *Rhodopseudomonas Palustris*, (b) *Blastochloris viridis*, and (c) *Bifidobacterium bifidum*) during irradiation with a near infrared laser [wavelength: 808 nm, output: 1.2 W (ca. 61.1 mW/mm$^2$), and irradiation time: 5 min] are shown in FIG. 5.

In the same manner as described above, changes in the temperatures of individual bacteria-dispersed solutions during irradiation with a near infrared laser [wavelength: 808 nm, output: 1.2 W (ca. 61.1 mW/mm$^2$), and irradiation time: 2 min] are shown in FIG. 28.

<Detection of Reactive Oxygen Species (ROS)>

In an ROS analysis, a 96-well plate (Thermo Fisher Scientific) having a transparent bottom portion and a black main body and Singlet Oxygen Sensor Green (SOSG) (Invitrogen) serving as a singlet oxygen detection reagent were used. A PBS buffer solution (100 μL, $5\times10^9$ CFU ml$^{-1}$), in which *R. Palustris* was dispersed, was diluted with a PBS buffer solution containing SOSG. The final concentrations of *R. Palustris* and SOSG in the reaction system were $1.3\times10^9$ CFU ml$^{-1}$ and 1 μM, respectively. Subsequently, a near infrared laser having a wavelength of 808 nm was applied to the sample at an output of 1.2 W (ca. 61.1 mW mm$^{-2}$) for 5 minutes. A PBS buffer solution that did not contain *R. Palustris* was used as a control. Green fluorescence correlating with ROS generation was measured using a microplate reader (Infinite 200 PRO M Plex) (excitation wavelength: 485 nm, fluorescence wavelength: 535 nm).

The behavior of generation of reactive oxygen species (ROS) singlet oxygen from an *R. Palustris*-dispersed solution during irradiation with a near infrared laser [wavelength: 808 nm, output: 1.2 W (ca. 61.1 mW/mm$^2$), and irradiation time: 5 min] is shown in FIG. 6.

<Cell Culture and Evaluation of Cytotoxicity>

Mouse colon cancer cells (Colon26) and human normal diploid fibroblasts (MRCS) were obtained from the Japanese Collection of Research Bioresources Cell Bank. Human lung adenocarcinoma epithelial cells (A549) and human colon adenocarcinoma (HT29) were purchased from DS Pharma Biomedical. Mouse macrophages (RAW264.7) were obtained from Riken Bio Resource Center. For the culture of Colon26, Roswell Park Memorial Institute (RPMI) 1640 Medium (Gibco), which was supplemented with 10% fetal bovine serum, 2 mM 1-glutamine, 1 mM sodium pyruvate, gentamycin, and penicillin-streptomycin (100 IU $ml^{-1}$), was used. Other cells were cultured in Dulbecco's Modified Eagle's Medium (DMEM) (Gibco), which was supplemented with 10% fetal bovine serum, 2 mM 1-glutamine, 1 mM sodium pyruvate, gentamycin, penicillin-streptomycin (100 IU $ml^{-1}$), and Hank's balanced salt solution (Life Technologies). The cells were cultured in a humidified chamber at 37 °C and in a 5% $CO_2$ atmosphere.

Cell viability was evaluated using Cell Counting Kit (CCK)-8 (Dojindo Laboratories) according to the manuals included therewith. The cells ($\times 10^3$ cells $well^{-1}$) were seeded on a 96-well plate, and were then incubated overnight. Subsequently, the cells were exposed to a bacteria-dispersed solution for 4 hours, and were then washed with a fresh culture solution. Thereafter, the resulting cells were incubated in a CCK-8 solution. Finally, the absorbance at 450 nm was measured using a microplate reader (Infinite 200 PRO M Plex; Tecan), so that the cell viability was calculated.

Evaluation of the cytotoxicity of the purple photosynthetic bacteria *R. Palustris* [the measurement of the cell viability of mouse colon cancer cells (Colon26), human lung adenocarcinoma epithelial cells (A549), human colon adenocarcinoma cells (HT29), and human normal diploid fibroblasts (MRCS), which were co-cultured with different concentrations of *R. Palustris* for 4 hours] is shown in FIG. 7. Individual graphs of FIG. 7 indicate MRCS, Colon26, A549 and HT29 from the left.

In the same manner as described above, the results obtained by evaluating the cytotoxicity of individual bacteria against mouse colon cancer cells (Colon26) [the measurement of the cell viability of mouse colon cancer cells (Colon26), which were co-cultured with different concentrations of individual bacteria for 4 hours] are shown in FIG. 29 to FIG. 31.

<Evaluation of Cell Viability by Laser Irradiation>

In order to evaluate the viability of cancer cells, Colon26, A549, and HT29 cells ($5\times 10^3$ cells/well) were seeded on a 96-well plate, and were then inoculated overnight. The cells were treated with a cell culture medium (100 μL) in which each different concentration (0.16, 0.31, 0.63, or $1.25\times 10^9$ CFU $ml^{-1}$) of *R. Palustris* was dispersed, or with a cell culture medium (100 μL) that did not contain such *R. Palustris*, and thereafter, a laser (wavelength: 808 nm, output: 1.2 W (ca. 61.1 mW $mm^{-2}$)) was applied to the cells for 5 minutes. After completion of the laser irradiation, the resulting cells were washed and were then incubated in a fresh medium. Using a CCK-8 kit, the samples immediately after the laser irradiation and that had been inoculated for 24 hours after the laser irradiation were examined in terms of cell viability.

Evaluation of the viability of various types of cancer cells, which were allowed to coexist with a control (a DMEM medium in which no bacteria were present) and with different concentrations of *R. Palustris*, and to which a near infrared laser [wavelength: 808 nm, output: 1.2 W (ca. 61.1 $mW/mm^2$), and irradiation time: 5 min] was applied, is shown in FIG. 8 [the cell viability was measured according to a WST-8 method 24 hours after completion of the laser irradiation].

<Fluorescence Observation of *R. Palustris* in Macrophage Cells>

RAW264.7 cells ($2.5\times 10^5$ cells $well^{-1}$) were seeded on a 24-well plate and were then incubated overnight. The cells were exposed to a cell culture medium ($1\times 10^8$ CFU) in which *R. Palustris* was dispersed, or to a culture medium containing no *R. Palustris*, and were then cultured for 2 hours under conditions of 37 °C and 5% $CO_2$. Thereafter, the cells were washed and were then incubated in a fresh medium for 4 hours. Thereafter, the cells were observed at room temperature using a fluorescence microscope system (IX73; Olympus) equipped with a near-infrared fluorescence mirror unit (IRDYE800-33LP-A-U01; Semrock) and an object lens (×60 magnification, aperture 1.35; UPLSAPO60X, Olympus).

The NIR-I fluorescence microscope image of mouse macrophages (RAW264.7) that were co-cultured with *R. Palustris* ($1\times 10^8$ CFU/mL) for 4 hours (wherein the white arrow indicates *R. Palustris* that did not lose a near-infrared fluorescence even after phagocytosis by the microphages) is shown in FIG. 21.

<In Vivo Anticancer Experiment and Toxicity Evaluation>

All animal experiments were carried out with the approval of Animal Care and Use Committee, Japan Advanced Institute of Science and Technology. Four-week-old female wild-type mice (n=10; average weight=15 g; BALB/cCrSlc) were purchased from Japan SLC, Inc., and were then acclimatized for 1 week. A mixed solution (v/v, 1:1) consisting of a Colon26 cell-dispersed solution ($1\times 10^6$ cells) (100 μL) and culture medium/Matrigel (Corning) was administered into two sites in the subcutis of lateral abdomen of each mouse, so as to produce colon cancer mouse models. Approximately 2 weeks later, *R. Palustris* ($1\times 10^9$ CFU $ml^{-1}$) or a PBS buffer solution was administered in an amount of 200 μL each into the caudal vein of each mouse which formed solid cancers (about 400 $mm^3$). Only to the solid cancer on the right side, a near infrared laser [wavelength: 808 nm, output (713 mW, 36.3 mW $mm^{-2}$)] was applied for 3 minutes at a pace of once two days. Using IR thermography (i7; FLIR, Nashua), the tumor surface temperature of the mouse during the laser irradiation was measured.

The measurement of the tumor surface temperature of Colon26 cancer-bearing mouse models during irradiation with a near infrared laser [wavelength: 808 nm, output: 0.9 W (ca. 45.9 $mW/mm^2$), and irradiation time: 3 min] [wherein the laser was applied 2 days after the administration of the bacteria (200 4, $1\times 10^9$ CFU) or PBS (200 μL) into the causal vein of each mouse] is shown in FIG. 9. Individual graphs of FIG. 9 indicate PBS, *R. Palustris*, PBS+Laser, and *R. Palustris*+Laser, from the left.

Observation of mouse behaviors and properties, the measurement of the size of a solid cancer, and transitions in mouse body weights were carried out once two days. Besides, the size of a solid cancer was calculated according to the following equation.

$$V=L\times W^2/2$$

In the above equation, V indicates the volume of a solid cancer, L indicates the length of a solid cancer, and W indicates the width of a solid cancer.

On the other hand, with regard to evaluation of the in vivo toxicity of *R. Palustris*, the in vivo toxicity was examined by performing a mouse blood test. Specifically, an *R. Palustris*-dispersed solution ($1\times 10^9$ CFU $ml^{-1}$) or a PBS buffer solution was administered in an amount of 200 μL each into the caudal vein of each 10-week-old female mice (n=5; average weight=21 g, BALB/cCrSlc, Japan SLC), and then, 7 days and 30 days after the administration, blood was collected from the abdominal aorta. Complete blood cell count (CBC) and biochemical tests were analyzed by Japan SLC, Inc. and Oriental Yeast Co., Ltd. The result of the CBC and the biochemical tests are shown in Table 1 and Table 2.

TABLE 1

Complete blood count (CBC) and biochemical parameters 7 days after administration of PBS or *R. Palustris* into mouse caudal vein

| Measured value | Entry | Unit | PBS (n = 5) | *R. Palustris* (n = 5) | P value |
|---|---|---|---|---|---|
| CBC | WBC | $\times 10^2\ \mu l^{-1}$ | 79.80 ± 12.02 | 66.8 ± 14.55 | >0.05 |
| | RBC | $\times 10^4\ \mu l^{-1}$ | 992.40 ± 43.97 | 934.2 ± 44.46 | >0.05 |
| | HGB | $g\ dl^{-1}$ | 15.32 ± 0.79 | 14.4 ± 0.69 | >0.05 |
| | HCT | % | 46.22 ± 2.25 | 43.26 ± 2.10 | >0.05 |
| | MCV | fl | 46.56 ± 0.56 | 46.32 ± 0.29 | >0.05 |
| | MCH | pg | 15.44 ± 0.24 | 15.4 ± 0.11 | >0.05 |
| | MCHC | $g\ dl^{-1}$ | 33.14 ± 0.12 | 33.3 ± 0.20 | >0.05 |
| | PLT | $\times 10^4\ \mu l^{-1}$ | 64.9 ± 2.65 | 61.10 ± 2.50 | >0.05 |
| Biochemical parameters | TP | $g\ dl^{-1}$ | 4.02 ± 0.11 | 4.14 ± 0.15 | >0.05 |
| | ALB | $g\ dl^{-1}$ | 2.72 ± 0.04 | 2.76 ± 0.09 | >0.05 |
| | BUN | $mg\ dl^{-1}$ | 20.70 ± 3.84 | 21.05 ± 3.45 | >0.05 |
| | CRE | $mg\ dl^{-1}$ | 0.12 ± 0.01 | 0.12 ± 0.01 | >0.05 |
| | Na | $mEq\ l^{-1}$ | 154.20 ± 1.10 | 154.00 ± 1.22 | >0.05 |
| | K | $mEq\ l^{-1}$ | 3.42 ± 0.36 | 3.78 ± 0.41 | >0.05 |
| | Cl | $mEq\ l^{-1}$ | 122.60 ± 0.89 | 123.80 ± 1.79 | >0.05 |
| | AST | $IU\ l^{-1}$ | 84.20 ± 13.26 | 88.60 ± 16.04 | >0.05 |
| | ALT | $IU\ l^{-1}$ | 58.60 ± 19.94 | 51.40 ± 8.20 | >0.05 |
| | LDH | $IU\ l^{-1}$ | 294.60 ± 38.82 | 342.00 ± 101.53 | >0.05 |
| | AMY | $IU\ l^{-1}$ | 1717.40 ± 110.16 | 1879.60 ± 265.61 | >0.05 |
| | CK | $IU\ l^{-1}$ | 180.80 ± 56.76 | 257.60 ± 139.97 | >0.05 |

The symbol "±" in the results indicates a standard deviation from 5 experiments.

Statistical analysis is carried out based on Student's t-test.

Abbreviations: ALB, albumin, ALT, alanine transaminase; AMY, amylase; AST, aspartate aminotransferase; BUN, blood urea nitrogen; Cl, chlorine; CK, creatine kinase; CRE, creatinine; CRP, C-reactive protein; HCT, hematocrit; HGB, hemoglobin: K, potassium; LDH, lactate dehydrogenase; MCH, mean corpuscular hemoglobin; MCHC, mean corpuscular hemoglobin concentration; MCV, mean corpuscular volume; Na, sodium; PLT, platelet; RBC, red blood cell; TP, total protein; WBC, white blood cell.

TABLE 2

CBC and biochemical parameters 30 days after administration of PBS or *R. Palustris* into mouse caudal vein

| Measured value | Entry | Unit | PBS (n = 5) | *R. Palustris* (n = 5) | P value |
|---|---|---|---|---|---|
| CBC | WBC | $\times 10^2\ \mu l^{-1}$ | 60.00 ± 6.81 | 64.20 ± 15.32 | >0.05 |
| | RBC | $\times 10^4\ \mu l^{-1}$ | 876.80 ± 27.06 | 892.00 ± 18.23 | >0.05 |
| | HGB | $g\ dl^{-1}$ | 13.44 ± 0.49 | 13.64 ± 0.50 | >0.05 |
| | HCT | % | 40.74 ± 1.38 | 41.54 ± 1.37 | >0.05 |
| | MCV | fl | 46.46 ± 0.39 | 46.56 ± 0.90 | >0.05 |
| | MCH | pg | 15.32 ± 0.29 | 15.28 ± 0.27 | >0.05 |
| | MCHC | $g\ dl^{-1}$ | 32.96 ± 0.45 | 32.84 ± 0.33 | >0.05 |
| | PLT | $\times 10^4\ \mu l^{-1}$ | 53.96 ± 5.96 | 53.98 ± 5.25 | >0.05 |
| Biochemical parameters | TP | $g\ dl^{-1}$ | 4.24 ± 0.13 | 4.12 ± 0.13 | >0.05 |
| | ALB | $g\ dl^{-1}$ | 2.76 ± 0.05 | 2.74 ± 0.05 | >0.05 |
| | BUN | $mg\ dl^{-1}$ | 15.20 ± 0.35 | 18.3 ± 3.04 | >0.05 |
| | CRE | $mg\ dl^{-1}$ | 0.08 ± 0.01 | 0.10 ± 0.02 | >0.05 |
| | Na | $mEq\ l^{-1}$ | 153.80 ± 0.84 | 154.00 ± 1.58 | >0.05 |
| | K | $mEq\ l^{-1}$ | 3.32 ± 0.40 | 3.16 ± 0.36 | >0.05 |
| | Cl | $mEq\ l^{-1}$ | 119.60 ± 1.14 | 120.50 ± 2.51 | >0.05 |
| | AST | $IU\ l^{-1}$ | 56.00 ± 3.54 | 66.60 ± 16.52 | >0.05 |
| | ALT | $IU\ l^{-1}$ | 35.80 ± 5.22 | 50.00 ± 14.66 | >0.05 |
| | LDH | $IU\ l^{-1}$ | 200.00 ± 30.20 | 249.80 ± 38.19 | >0.05 |
| | AMY | $IU\ l^{-1}$ | 1649.40 ± 135.58 | 1967.00 ± 317.93 | >0.05 |
| | CK | $IU\ l^{-1}$ | 118.00 ± 34.55 | 160.40 ± 65.49 | >0.05 |

The symbol "±" in the results indicates a standard deviation from 5 experiments.

Statistical analysis is carried out based on Student's t-test.

Abbreviations: ALB, albumin, ALT, alanine transaminase; AMY, amylase; AST, aspartate aminotransferase; BUN, blood urea nitrogen; Cl, chlorine; CK, creatine kinase; CRE, creatinine; CRP, C-reactive protein; HCT, hematocrit; HGB, hemoglobin: K, potassium; LDH, lactate dehydrogenase; MCH, mean corpuscular hemoglobin; MCHC, mean corpuscular hemoglobin concentration; MCV, mean corpuscular volume; Na, sodium; PLT, platelet; RBC, red blood cell; TP, total protein; WBC, white blood cell.

<Colony Count>

Into the causal vein of colon cancer-bearing mouse models (female, 8 weeks; n=5; average weight=19 g; average tumor size: about 400 $mm^3$; BALB/cCrSIc; Japan SLC) into which Colon26 had been seeded, *R. Palustris* ($5\times10^9$ CFU $ml^{-1}$), *B. viridis* ($5\times10^9$ CFU $ml^{-1}$), and a cell culture medium were each administered in an amount of 200 μL. Thereafter, 1, 24, 48, and 144 hours after the administration, individual tissues and tumors were excised and cleaved, and then, the weights thereof were measured. Using a pestle, the excised matters were each homogenized at a temperature of 4 °C in a PBS buffer solution, and the obtained mixture was then shaken at 15 °C at a rate of 380 rpm min-1 for 20 minutes. Thereafter, the supernatant was 10-fold diluted with a PBS buffer solution, and each sample (1004) was then seeded on an agar medium, followed by performing an anaerobic culture for 7 days. The number of the formed bacterial colonies was manually measured.

Evaluation of the antitumor activity of *R. Palustris* driven by a near infrared light [wherein PBS (200 μL) or an *R. Palustris*-dispersed solution (200 μL, 1×10$^9$ CFU) was administered into the caudal vein of the mice, and the laser was then applied only to the tumor on the right side of the mice (wavelength: 808 nm, output: 0.9 W (ca. 45.9 mW/mm$^2$), and irradiation time: 3 min); the black arrow in the graph indicates the day on which the bacteria or PBS was administered, and the red arrow indicates the day of the laser irradiation, respectively] is shown in FIG. 10.

Photographs of the mice subjected to individual treatments (wherein the arrow indicates each tumor irradiated with the laser) are shown in FIG. 11.

A photograph of tumors excised 34 days after various types of treatments were performed is shown in FIG. 12.

The survival percentage of the mice under individual treatments for 34 days is shown in FIG. 13.

A photograph of red colonies derived from *R. Palustris* that has specifically grown in a tumor (wherein various types of organs and a tumor were excised 2 days after administration of *R. Palustris* (200 μL, 1×10$^9$ CFU/mL) into the caudal vein of Colon26 cancer-bearing mouse models, and the extracts thereof were then applied onto an agar medium, followed by performing a culture under anaerobic conditions) is shown in FIG. 15.

The number of surviving cells of *R. Palustris* in various types of organs and a tumor [wherein various types of organs and a tumor were excised 7 days after administration of *R. Palustris* (200 μL, 1×10$^9$ CFU/mL) into the caudal vein of Colon26 cancer-bearing mouse models, and the extracts thereof were then applied onto an agar medium, followed by performing a culture under anaerobic conditions] is shown in FIG. 16.

The fluorescent intensity derived from *R. Palustris* in various types of organs and a tumor [wherein *R. Palustris* (200 μL, 1×10$^9$ CFU/mL) was administered into the caudal vein of Colon26 cancer-bearing mouse models, and fluorescence bioimaging analysis was then performed over time, and the fluorescent intensity was then measured] is shown in FIG. 17.

The number of surviving cells of *R. Palustris* in various types of organs and a tumor [wherein various types of organs and a tumor were excised over time, after administration of *R. Palustris* (200 4, 1×10$^9$ CFU/mL) into the caudal vein of Colon26 cancer-bearing mouse models, then, the extract was applied onto an agar medium, followed by performing a culture under anaerobic conditions, and the number of colonies formed was then measured] is shown in FIG. 18.

A photograph of green colonies derived from *Blastochloris viridis* that has specifically grown in a tumor [wherein various types of organs and a tumor were excised 2 days after administration of *Blastochloris viridis* (200 4, 1×10$^9$ CFU/mL) into the caudal vein of Colon26 cancer-bearing mouse models, and the extracts thereof were then applied onto an agar medium, followed by performing a culture under anaerobic conditions] is shown in FIG. 19.

The number of surviving cells of *Blastochloris viridis* in various types of organs and a tumor [wherein various types of organs and a tumor were excised 7 days after administration of *Blastochloris viridis* (200 4, 1×10$^9$ CFU/mL) into the caudal vein of Colon26 cancer-bearing mouse models, and the extracts thereof were then applied onto an agar medium, followed by performing a culture under anaerobic conditions] is shown in FIG. 20.

<In Vivo Fluorescence Bioimaging>

In order to measure the biodistribution of bacteria using NIR-I fluorescence, into the caudal vein of Colon26 colon cancer-bearing mouse models (female; 8 weeks; n=3; average weight=19 g; average tumor size=430 mm$^3$; BALB/cCrSIc; Japan SLC), a cell culture medium comprising *R. Palustris* (200 4, 1×10$^9$ CFU) or a PBS buffer solution comprising no bacteria was administered. Near infrared fluorescence images of mice and main biological tissues were observed using VISQUE™ InVivo Smart-LF (Vieworks). The excitation wavelength and the fluorescence wavelength were $\lambda_{ex}$=740 to 790 nm and $\lambda_{em}$=810 to 860 nm, respectively. Moreover, for the image analysis, CleVue™ software (Vieworks) was used.

In vivo near infrared I region (NIR-I) fluorescence bioimaging (Ex: 740 nm to 790 nm, and Em: 810 nm to 860 nm) of Colon26 cancer-bearing mouse models [wherein the images were photographed 5 days after administration of *R. Palustris* (200 μL, 1×10$^9$ CFU/mL) or PBS (200 μL) into the caudal vein of the mice; the arrow indicates the position of the tumor) is shown in FIG. 14.

NIR-II fluorescence bioimaging was carried out by Summit Pharmaceuticals International. Into the solid cancer of HT29 human colon adenocarcinoma mouse models (female; 10 weeks; n=3; average weight=21 g; average tumor size=100 mm$^3$; BALB/cSlc-nu/nu; Japan SLC), a PBS buffer solution containing *B. viridis* (20 μL, 1×10$^8$ CFU) was administered. *B. viridis*-derived NIR-II fluorescence was observed using SAI-1000 (Shimazu) under conditions of a laser output of 2 W and an exposure time of 200 msec.

Angiography using *B. viridis*-derived NIR-II fluorescence was carried out by administering a PBS buffer solution containing *B. viridis* (200 μL, 1×10$^9$ CFU) into the causal vein of the same HT29 human colon adenocarcinoma mouse models (n=3) as described above, and then using the same system as described above (laser output=10 W, and an exposure time=400 msec).

Angiography according to near infrared II region (NIR-II) fluorescence bioimaging using *Blastochloris viridis* (Ex: 980 nm, Em: 1000 nm to 1700 nm) [wherein *B. viridis* (200 μL, 10$^9$ CFU) was administered into the caudal vein of nude mice, followed by photographing) is shown in FIG. 23.

<In Vivo Photoacoustic (PA) Imaging>

PA imaging was carried out by Summit Pharmaceuticals International using multi spectral optoacoustic tomography (MSOT) inVision 256-TF system (SYS-MSOTiV256TF; iThera Medical). A PBS buffer solution, in which *R. Palustris* (20 μL, 1×10$^8$ CFU) had been dispersed, was administered into the solid cancer of HT29 human colon adenocarcinoma mouse models (female; 10 weeks; n=3; average weight=21 g; average tumor size=100 mm$^3$; BALB/cSlc-nu/nu; Japan SLC) to obtain a PA image.

The photoacoustic (PA) imaging of a mouse tumor using *R. Palustris* [wherein PBS (20 μL) (left side of the photograph) and *R. Palustris* (20 μL, 10$^8$ CFU/mL) (right side of the photograph) were each administered into the tumor of an HT29 cancer-bearing mouse model, followed by photographing) is shown in FIG. 22.

<Statistical Analysis of Data>

The symbol "±" in the data indicates of a standard deviation, and "n" indicates the number of samples. For the statistical analysis of the data, Student's t-test was used. *, , and * indicate the p values of <0.05, <0.005, and <0.001, respectively.

The invention claimed is:

1. A method for treating cancer, comprising administering photosynthetic bacteria to a subject, and applying light irradiation to the subject, to which the photosynthetic bacteria is administered, wherein the light irradiation is irradiation with a near infrared light, and wherein the photosynthetic bacteria are *Rhodopseudomonas palustris*.

* * * * *